US009804175B2

(12) United States Patent
Attur et al.

(10) Patent No.: US 9,804,175 B2
(45) Date of Patent: Oct. 31, 2017

(54) METHODS AND KITS FOR DIAGNOSING OSTEOARTHRITIS AND PREDICTING PROGRESSION

(71) Applicant: New York University, New York, NY (US)

(72) Inventors: Mukundan Attur, Woodside, NY (US); Steven B. Abramson, Rye, NY (US)

(73) Assignee: New York University, New York, NY (US)

( * ) Notice: Subject to any disclaimer, the term of this patent is extended or adjusted under 35 U.S.C. 154(b) by 61 days.

(21) Appl. No.: 14/542,757

(22) Filed: Nov. 17, 2014

(65) Prior Publication Data
US 2015/0072364 A1 Mar. 12, 2015

Related U.S. Application Data

(62) Division of application No. 13/232,715, filed on Sep. 14, 2011, now Pat. No. 8,889,367.

(60) Provisional application No. 61/382,717, filed on Sep. 14, 2010.

(51) Int. Cl.
G01N 33/00 (2006.01)
C12Q 1/00 (2006.01)
G01N 33/74 (2006.01)
C12Q 1/68 (2006.01)

(52) U.S. Cl.
CPC .......... G01N 33/74 (2013.01); C12Q 1/6883 (2013.01); C12Q 2600/118 (2013.01); C12Q 2600/158 (2013.01); G01N 2333/475 (2013.01); G01N 2333/52 (2013.01); G01N 2333/545 (2013.01); G01N 2333/964 (2013.01); G01N 2333/96494 (2013.01); G01N 2800/105 (2013.01); G01N 2800/56 (2013.01)

(58) Field of Classification Search
None
See application file for complete search history.

(56) References Cited

U.S. PATENT DOCUMENTS

| 7,662,573 | B2 | 2/2010 | Ling et al. |
| 2003/0202977 | A1 | 10/2003 | Amin et al. |
| 2007/0225206 | A1 | 9/2007 | Ling et al. |
| 2010/0129798 | A1 | 5/2010 | Abramson et al. |

OTHER PUBLICATIONS

Riyazi et al. Association of the Risk of Osteoarthritis With High Innate Production of Interleukin-1β and Low Innate Production of Interleukin-10 Ex Vivo, Upon Lipopolysaccharide Stimulation. May 2005. Arthritis & Rheumatism. vol. 52, No. 5, pp. 1443-1450.*
Jung et al. Blood specimen collection methods influence the concentration and of the diagnostic validity of matrix metalloproteinase 9 in blood. 2001. Clinica Chimic Acta. vol. 314, pp. 241-244.*
Piperno et al. Quantitative evaluation of joint space width in fermororbital osteoarthritis: comparison of three radiographic views. 1998. Osteoarthritis and Cartilage. vol. 6, p. 252-259.*

Abramson, et al. Prospects for disease modification in osteoarthritis, Nat Clin Pract Rheumatol, vol. 2, No. 6, pp. 304-312, 2006.
Abramson, et al., Developments in the scientific understanding of osteoarthritis, Arthritis Res Ther, vol. 11, No. 3, p. 227-236, 2009.
Attur, et al. Prostaglandin E2 exerts catabolic effects in osteoarthritis cartilage: evidence for signaling via the EP4 receptor, J Immunol, vol. 181, pp. 5082-5088, 2008.
Attur, et al., Increased interleukin-1β gene expression in peripheral blood leukocytes is associated with increased pain and predicts risk for progression of symptomatic knee osteoarthritis, Arthritis Rheum, vol. 63, No. 7, pp. 1908-1917, 2011.
Attur, et al., Genetic markers associated with generalized osteoarthritis (GOA), Osteoarthritis Cartilage, vol. 16, Suppl. 4, p. S158, 2008.
Attur, et al., Activation of diverse eicosanoid pathways in osteoarthritic cartilage: a lipidomic and genomic analysis, Bull NYU Hosp Jt Dis, vol. 70, No. 2, pp. 99-108, 2012.
Attur, et al., PGE2 attenuates aggrecan gene expression and accelerates aggrecan degradation via activation of ADAMTS in OA chondrocytes, Osteoarthritis Cartilage, vol. 15, Suppl. 3, pp. C102-C103, 2007.
Attur, et al., Association of interleukin-1 receptor antagonist (IL-1RN) TTG haplotype with radiographic knee OA severity in large scale meta-analysis, abstract, Osteoarthritis Cartilage, vol. 18, Suppl. 2, p. S172, Abstract 391, 2010.
Attur, et al., Interleukin-1 receptor antagonist gene variations predict the severity and progression of knee osteoarthritis, abstract, Osteoarthritis Cartilage, vol. 18, Suppl. 2, p. S172, Abstract 392, 2010.
Attur M, et al., Elevated levels of inflammatory mediator prostaglandin E2 (PGE2) in ex-vivo cultured peripheral blood leukocytes (PBL) of osteoarthritis (OA) patients, Osteoarthritis Cartilage, vol. 16, Suppl. 4, p. S191, 2008.
Attur, et al., Prognostic biomarkers in osteoarthritis, Curr Opin Rheumatol, vol. 25, No. 1, pp. 136-144, 2013.
Attur, et al., Radiographic severity of knee osteoarthritis is conditional on interleukin 1 receptor antagonist gene variations, Ann Rheum Dis, vol. 69, No. 5, pp. 856-861, 2010.
Attur, et al., Osteoarthritis or osteoarthrosis: the definition of inflammation becomes a semantic issue in the genomic era of molecular medicine, Osteoarthritis Cartilage, vol. 10, No. 1, pp. 1-4, 2002.
Attur, et al., Reversal of autocrine and paracrine effects of interleukin 1 (IL-1) in human arthritis by type II IL-1 decoy receptor. Potential for pharmacological intervention, J Biol Chem, vol. 275, pp. 40307-40315, 2000.
Attur, et al., Functional genomics approaches in arthritis, Am J Pharmacogenomics, vol. 4, No. 1, pp. 29-43, 2004.
Attur, et al., Functional genomic analysis of type II IL-1β decoy receptor: potential for gene therapy in human arthritis and inflammation,J Immunol., vol. 168, No. 4, pp. 2001-2010, 2002.
Attur, et al., "A system biology" approach to bioinformatics and functional genomics in complex human diseases: arthritis, Curr Issues Mol Biol, vol. 4, No. 4, pp. 129-146, 2002.
Bauer, et al., Classification of osteoarthritis biomarkers: a proposed approach, Osteoarthritis Biomarkers Network, Osteoarthritis Cartilage, vol. 14, No. 8, pp. 723-727, 2006.
Berenbaum, Osteoarthritis as an inflammatory disease (osteoarthritis is not osteoarthrosis!), Osteoarthritis and Cartilage pp. 16-21, 2013.
Blood, Miller-Keane Encyclopedia and Dictionary of Medicine, Nursing, and Allied Health, Seventh Edition 2003, Saunders, 8 pages.

(Continued)

Primary Examiner — Channing S Mahatan
(74) Attorney, Agent, or Firm — Troutman Sanders LLP

(57) ABSTRACT

This disclosure relates to methods and kits for diagnosing osteoarthritis and for determining the progression of osteoarthritis in a subject.

23 Claims, 9 Drawing Sheets

(56) References Cited

OTHER PUBLICATIONS

Bukowski, et al., IL-1 RN polymorphisms are associated with radiographic severity in osteoarthritis, Osteoarthritis Cartilage, vol. 16, Suppl. 4, p. S34, 2008.
Jonsson, et al., Increased levels of leukocyte-derived MMP-9 in patients with stable angina pectoris, PLoS One, vol. 6, No. 4, pp. e19340-7, 2011.
Kerkhof, et al., Large-scale meta-analysis of interleukin-1 beta and interleukin-1 receptor antagonist polymorphisms on risk of radiographic hip and knee osteoarthritis and severity of knee osteoarthritis, Osteoarthritis Cartilage, vol. 19, pp. 265-271, 2011.
Krasnokutsky, et al., Current concepts in the pathogenesis of osteoarthritis, Osteoarthritis Cartilage, vol. 16 , Suppl. 3, pp. S1-S3, 2008.
Krasnokutsky, et al., Quantitative MRI evidence of synovial proliferation is associated with radiographic severity of knee osteoarthritis, Arthritis Rheum, vol. 63, No. 10, pp. 2983-2991, 2011.
Kraus, et al., Association of bone scintigraphic abnormalities with knee malalignment and pain, Ann Rheum Dis, vol. 68, pp. 1673-1679, 2009.
Lai, et al., Enhanced COMP catabolism detected in serum of patients with arthritis and animal models through a novel capture ELISA, Osteoarthritis Cartilage, vol. 20, pp. 854-862, 2012.
Maloney et al. Inflammatory Agonists Induce Cyclooxygenase Type 2 Expression by Human Neutrophils, J. Immunology vol. 160, pp. 1402-1410.
Lee, et al., Selective inhibition of prostaglandin E2 receptors EP2 and EP4 inhibits invasion of human immortalized endometriotic epithelial and stromal cells through suppression of metalloproteinases, Mol Cell Endocrinol, vol. 332, pp. 306-313, 2011.
Nemirovskiy, et al., Predicting radiographic joint space narrowing (JSN) using biomarkers for osteoarthritis (OA) clinical trials, Osteoarthritis Cartilage, vol. 16, Suppl. 4, pp. S56-S57, 2008.
Partial Office Action from U.S. Appl. No. 11/573,711, including reasons for allowance dated Oct. 2, 2009/, 3 pages.
Pelletier, et al., Osteoarthritis, an inflammatory disease. Potential implication for the selection of new therapeutic targets, Arthritis Rheum, vol. 44, No. 6, pp. 1237-1247, 2001.
Regatte, et al., Bone marrow changes (edema and fatty infiltration) on MRI predict radiographic severity of knee OA, Osteoarthritis Cartilage, vol. 15, Suppl. C, p. C180, 2007.
Ryan et al., Activated Human B Lymphocytes Express Cyclooxygenase-2 and Cyclooxygenase Inhibitors Attenuate Antibody Production, J. Immunology vol. 174, pp. 2619-2626, 2005.
Simon, et al., Pitfalls in the use of DNA microarray data for diagnostic and prognostic classification, J Natl Cancer Inst, vol. 95, No. 1, pp. 14-18, 2003.
Spencer, et al. Subcellular Localization of Prostaglandin Endoperoxide H Synthases-1 and -2 by Immunoelectron Microscopy, J. Biol. Chem. vol. 273, pp. 9886-9893, 1998.
Kellgren et al., Radiological Assessment of Osteo-Arthrosis, Ann Rheum Dis 16: 494-502. (1952).
Davis et al., Obesity and Osteoarthritis of the Knee: Evidence From the National Health and Nutrition Examination Survey (NHANES I), Seminars in Arthritis and Rheumatism 20(3) Suppl 1: 34-41. (1990).
Kellgren, J. H., et al, "Radiological Assessment of Osteo-Arthrosis", Ann. Rheum. Dis. (1957), vol. 16, pp. 494-502.
The Osteoarthritis Initiative, Operational Manual, Biospecimen Collection (OAI), Version 1.6p (2009), 72 pages.

* cited by examiner

METHODS AND KITS FOR DIAGNOSING OSTEOARTHRITIS AND PREDICTING PROGRESSION

CROSS REFERENCE TO RELATED APPLICATIONS

This application is a divisional of U.S. patent application Ser. No. 13/232,715 filed on Sep. 14, 2011 and claims the benefit of priority to U.S. Provisional Patent Application No. 61/382,717 filed on Sep. 14, 2010, the entire contents of which applications are hereby incorporated by reference.

FEDERALLY SPONSORED RESEARCH OR DEVELOPMENT

This invention was made with government support under Grant No. AR052873, awarded by the National Institutes of Health. The government has certain rights in the invention.

TECHNICAL FIELD

This disclosure generally relates to methods and kits for diagnosing and predicting progression of osteoarthritis.

BACKGROUND

Osteoarthritis (OA) is the most common adult joint disease. The frequency and severity of OA is increasing in all aging populations, with an estimated prevalence in the US of more than 25 million affected adults (Lawrence et al., Arthritis Rheum 2008; 58:26-35). Disease progression is associated with cartilage degradation, joint space narrowing (JSN), and loss of function. While radiographic progression has highlighted JSN, the emergence of magnetic resonance imaging has underscored the involvement of multiple joint tissues in OA, particularly subchondral bone, menisci, and synovium (Abramson and Attur, Arthritis Res Ther 2009; 11:227). The etiology of osteoarthritis is multifactorial involving both mechanical and biochemical factors. Osteoarthritis commonly affects the hands, feet, spine, and large extraspinal, weight-bearing joints, such as the hips and knees. The joints predominantly involved by osteoarthritis are weight bearing and include the knees, hips, cervical and lumbosacral spine, and feet. Other commonly affected joins include the distal interphalangeal (DIP) and proximal interphalangeal (PIP) joints of the hands. Primary osteoarthritis generally refers to osteoarthritis of no known cause. Secondary osteoarthritis generally refers to osteoarthritis resulting from some external or internal injury or disease (obesity, repeated trauma or surgery to the joint structures, abnormal joints at birth (congenital abnormalities), gout, diabetes and other hormone disorders). Generalized osteoarthritis affects many joints. Localized osteoarthritis typically affects a single joint, though in some cases, such as with finger arthritis, several joints may be affected. Accordingly, localized osteoarthritis may be said to affect the joints of one site.

Although OA has traditionally been considered a noninflammatory joint disease, it is now well-appreciated that mediators of inflammation are produced by articular tissues in OA and have been implicated in disease pathogenesis (Attur et al., J Biol Chem 2000; 275:40307-15; Pelletier et al., Arthritis Rheum 2001; 44:1237-47).

SUMMARY

To allow for more efficient osteoarthritis (OA) treatment and delay of OA progression, there is currently a great need in methods for earlier diagnosis of OA and methods for identifying patients who are at higher risk of OA progression. The present invention addresses these and other needs by providing new methods for OA diagnosis and progression and associated kits and compositions.

In one aspect, the invention provides a method of diagnosing osteoarthritis in a subject, comprising the steps of:
(a) determining the expression levels of JunB, MMP-9, TGFβ-1, lamin A/C, granulin, small inducible cytokine A3, and chemokine receptor 1 genes in peripheral blood leukocytes (PBL) from the subject;
(b) comparing the expression level of each gene determined in step (a) with a corresponding control expression level for that gene, and
(c) (i) identifying the subject as being afflicted with osteoarthritis when the expression level of each of JunB, MMP-9, TGFβ-1, lamin A/C, granulin, small inducible cytokine A3, and chemokine receptor 1 genes in step (a) is increased by at least 1.5 fold as compared to the corresponding control expression level or (ii) identifying the subject as not being afflicted with osteoarthritis when the expression level of each of JunB, MMP-9, TGFβ-1, lamin A/C, granulin, small inducible cytokine A3, and chemokine receptor 1 genes in step (a) is not increased or is increased by less than 1.5 fold as compared to the corresponding control expression level.

In another aspect, the invention provides a method of diagnosing osteoarthritis in a subject, comprising the steps of:
(a) determining the expression level of one or more genes selected from the group consisting of IL-6, IL-8 and COX-2 in peripheral blood leukocytes (PBL) from the subject;
(b) comparing the expression level(s) determined in step (a) with a corresponding control expression level(s) of the same gene(s), and
(c) identifying the subject as being afflicted with osteoarthritis when the expression level of IL-6 gene in step (a) is increased by at least 1.5 fold or the expression level of IL-8 gene in step (a) is increased by at least 2 fold or the expression level of COX-2 gene in step (a) is increased by at least 2 fold as compared to the corresponding control expression level.

In a further aspect, the invention provides a method of determining whether a subject diagnosed with osteoarthritis is at increased risk for progression to severe osteoarthritis within 12-24 months (e.g., as measured by a decrease in joint space width (JSW) or joint space narrowing (JSN)) or is at increased risk for developing increased pain, said method comprising the steps of:
(a) determining the expression levels of one or more genes selected from the group consisting of TNF-1θ, and COX-2 in peripheral blood leukocytes (PBL) from the subject;
(b) comparing the expression level(s) determined in step (a) with a corresponding control expression level(s) of the same gene(s), and
(c) identifying the subject as being at increased risk for progression to severe osteoarthritis within 12-24 months or as being at increased risk for developing increased pain when the expression level of one or more genes selected from the group consisting of IL-1θ, TNF-I, and COX-2 in step (a) is increased by at least 2 fold as compared to the corresponding control expression level(s).

In one embodiment, the above prognostic method further comprises the steps of:

(d) determining the total MMP-9 (tMMP-9, including both pro and active form of MMP-9) protein level in a blood plasma sample from the subject;

(e) (e) comparing the plasma level of tMMP-9 protein determined in step (d) with a control plasma level of tMMP-9 protein (e.g., the plasma level of tMMP-9 protein in a similarly processed blood plasma sample from a control subject or a predetermined standard), and (f) identifying the subject as being at increased risk for progression to severe osteoarthritis within 12-24 months or as being at increased risk for developing increased pain when the plasma level of tMMP-9 protein in step (d) is increased by at least 2 fold as compared to the control plasma level of tMMP-9 protein.

The corresponding control gene expression level used in any of the above methods of the invention can be the expression level of the same gene in similarly processed peripheral blood leukocytes (PBL) from a control subject (e.g., BMI-, age-, and gender-matched subject without OA as determined by both radiographic and symptomatic examination) or a predetermined standard.

Each of the above methods of the invention can also comprise a step of obtaining peripheral blood leukocytes (PBL) from the subject prior to step (a).

Non-limiting examples of the methods for determining gene expression level useful in any of the above methods of the present invention include polymerase-based assays, hybridization-based assays, flap-endonuclease-based assays, and direct mRNA capture.

An yet another aspect, the invention provides a method of determining whether a subject diagnosed with osteoarthritis is at increased risk for progression to severe osteoarthritis within 12-24 months, said method comprising the steps of:

(a) determining in a blood plasma sample from the subject the level of one or more protein(s) selected from the group consisting of total MMP-9 (tMMP-9, including both pro and active form of MMP-9), proMMP-9 (pMMP-9), VEGF, and IL1-Ra;

(b) comparing the plasma level(s) determined in step (a) with a corresponding control plasma level(s) of the same protein(s), and (c) identifying the subject as being at increased risk for progression to severe osteoarthritis within 12-24 months when the plasma level of one or more protein(s) selected from the group consisting of total MMP-9 (tMMP-9), proMMP-9 (pMMP-9), VEGF, and IL1-Ra in step (a) is increased by at least 2 fold as compared to the corresponding control plasma level(s).

The corresponding control plasma level of protein can be the plasma level of the same protein in a similarly processed blood plasma sample from a control subject (e.g., BMI-, age-, and gender-matched subject without OA as determined by both radiographic and symptomatic examination) or a predetermined standard. In one embodiment, the plasma level of protein(s) is determined using ELISA. In one embodiment, the method comprises obtaining a blood plasma sample from the subject prior to step (a).

The methods of the invention can be used for diagnosis or prognosis of osteoarthritis (OA) in various subjects, including humans, veterinary animals and experimental animal models of OA. In a preferred embodiment, the subject is a human.

The methods of the invention can be used for diagnosis or prognosis of osteoarthritis of various joints. In a preferred embodiment, the osteoarthritis is a knee osteoarthritis.

In conjunction with the above methods, the invention also provides various kits and compositions.

In one embodiment, the invention provides a kit for diagnosing osteoarthritis in a subject, said kit comprising pairs of oligonucleotides directed toward each of JunB, MMP-9, TGFθ-1, lamin A/C, granulin, small inducible cytokine A3, and chemokine receptor 1, wherein said pairs of oligonucleotides can be used to determine the expression levels of JunB, MMP-9, TGFθ-1, lamin A/C, granulin, small inducible cytokine A3, and chemokine receptor 1.

In another embodiment, the invention provides a kit for diagnosing osteoarthritis in a subject, said kit comprising pair(s) of oligonucleotides directed toward at least one of IL-6, IL-8 and COX-2, wherein said pair(s) of oligonucleotides can be used to determine the expression levels of one or more of IL-6, IL-8 and COX-2.

In a further embodiment, the invention provides a kit for prognosis of osteoarthritis in a subject, said kit comprising pair(s) of oligonucleotides directed toward at least one of IL-1β, TNF-α and COX-2, wherein said pair(s) of oligonucleotides can be used to determine the expression levels of one or more of IL-1β, TNF-α and COX-2.

Any of the above kits can also include (i) a detection means and/or (ii) an amplification means and/or (iii) a pair of control oligonucleotides.

In one embodiment, the prognostic kit comprising pair(s) of oligonucleotides directed toward at least one of IL-1β, TNF-α and COX-2 further comprises antibodies for detecting tMMP-9 protein.

In a separate embodiment, the invention provides a kit for prognosis of osteoarthritis in a subject, said kit comprising antibodies for detecting one or more protein(s) selected from the group consisting of total MMP-9 (tMMP-9), proMMP-9 (pMMP-9), VEGF, and IL1-Ra.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DETAILED DESCRIPTION OF THE INVENTION

Figure 1:
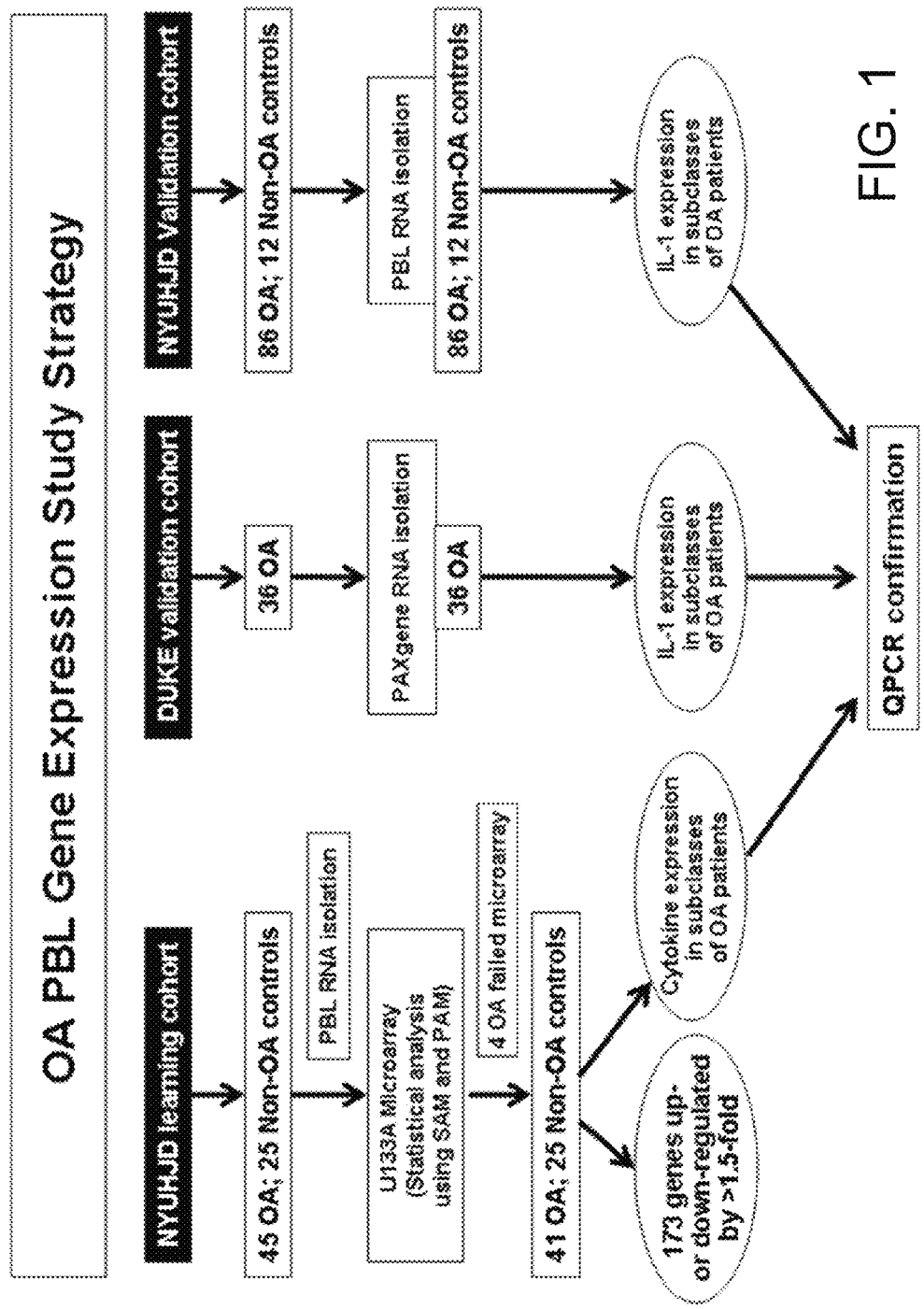
FIG. 1 is a schematic showing the OA PBL gene expression study strategy.

Methods for diagnosing osteoarthritis (OA) and for predicting the progression of OA are described herein. These methods include determining the expression levels of particular genes in peripheral blood leukocytes (PBL) and/or determining the level of certain proteins in a blood plasma sample from a subject having or suspected of having osteoarthritis. A diagnosis of osteoarthritis may be made, or the risk for progression of osteoarthritis may be determined depending on increase in the marker level as compared to a control.

The term "a control level" as used herein encompasses predetermined standards (e.g., a published value in a reference) as well as levels determined experimentally in similarly processed samples from control subjects (e.g., BMI-, age-, and gender-matched subjects without OA as determined by both radiographic and symptomatic examination).

As used herein, the term "similarly processed" refers to samples (e.g., peripheral blood leukocytes or blood plasma samples) which have been obtained using the same protocol.

An "individual" or "subject" or "animal", as used herein, refers to humans, veterinary animals (e.g., cats, dogs, cows, horses, sheep, pigs, etc.) and experimental animal models of OA. In a preferred embodiment, the subject is a human.

Peripheral blood leukocytes (PBL) can be obtained from an individual in the form of a Peripheral Blood Mononuclear Cell (PBMC) sample. PBMCs are a mixture of monocytes and lymphocytes, and there are a number of known methods for isolating PBMCs from whole blood. While any suitable method may be employed, in one embodiment, PBMCs are isolated from whole blood samples using density gradient centrifugation. Alternatively, PBL may be further isolated from whole blood or PBMCs to yield a cell subpopulation, such as a population of lymphocytes (e.g., T-lymphocytes or sub-population thereof). Examples for isolating such sub-populations are known in the art, and include cell sorting or cell-capturing using antibodies to particular cell-specific markers. In another embodiment, PBL can be obtained from whole blood using the PAXgene kit (Qiagen).

RNA can be extracted from the collected cells (e.g., from PBMC or PBL samples or from blood plasma) by any known method. For example, RNA may be purified from cells using a variety of standard procedures as described, for example, in *RNA Methodologies, A laboratory guide for isolation and characterization,* 2nd edition, 1998, Robert E. Farrell, Jr., Ed., Academic Press. In addition, various commercial products are available for RNA isolation. As would be understood by those skilled in the art, total RNA or polyA+ RNA may be used for preparing gene expression profiles.

The expression levels (or expression profile) can be then determined using any of various techniques known in the art and described in detail elsewhere. Such methods generally include, without limitation, polymerase-based assays such as RT-PCR (e.g., TAQMAN), hybridization-based assays such as DNA microarray analysis, flap-endonuclease-based assays (e.g., INVADER), and direct mRNA capture (QUANTIGENE or HYBRID CAPTURE (Digene)). See, for example, US 2010/0190173 for descriptions of representative methods that can be used to determine expression levels.

As used herein, the term "gene" refers to a DNA sequence expressed in a sample as an RNA transcript. As used herein, "differentially expressed" means that the level or abundance of an RNA transcripts (or abundance of an RNA population sharing a common target sequence (e.g., splice variant RNAs)) is higher or lower by at least a certain value in a test sample as compared to a control level. For example, the level of the RNA or RNA population may be higher or lower by at least 1.5 to two-fold as compared to a control level.

In various embodiments disclosed herein, the expression levels of different combinations of genes can be used to glean different information. For example, increased expression levels of JunB, MMP-9, TGFθ-1, lamin A/C, granulin, small inducible cytokine A3, and chemokine receptor 1 in an individual as compared to a control is indicative of a diagnosis of osteoarthritis. In another embodiment, increased expression levels of at least one gene selected from the group consisting of IL-6, IL-8 and COX-2 in an individual as compared to a control is indicative of a diagnosis of osteoarthritis. In yet another embodiment, increased expression levels of at least one gene selected from the group consisting of IL-1β, TNF-α and COX-2 in an individual as compared to a control can be used to determine whether or not said individual is at increased risk for progression to severe osteoarthritis within 12-24 months (e.g., as measured by a decrease in joint space width (JSW) or joint space narrowing (JSN)) or is at increased risk for developing increased pain.

In some embodiments, the plurality of genes are differentially expressed in osteoarthritic patients with respect to control by a fold change magnitude of at least 1.5, or at least about 1.7, or at least about 2, or at least about 2.5. Alternatively, the expression levels may differ by at least about 3- or 5-, 10-fold, or more.

After determining the expression levels of the appropriate combination of genes in a patient's PBL, the patient can be classified as having osteoarthritis. The classification may be determined computationally based upon known methods as described herein. The result of the computation may be displayed on a computer screen or presented in a tangible form, for example, as a probability (e.g., from 0 to 100%) of the patient having osteoarthritis. The report will aid a physician in diagnosis or treatment of the patient. For example, in certain embodiments, the patient's expression levels will be diagnostic of osteoarthritis or prognostic of increased risk for progression to severe osteoarthritis or prognostic of increased risk for developing increased pain, and the patient will be subsequently treated as appropriate. In other embodiments, the patient's expression levels of the appropriate combination of genes will not be increased, thereby allowing the physician to exclude osteoarthritis as a diagnosis.

Further provided are kits containing nucleic acid oligonucleotides for determining the level of expression of a particular combination of genes in a patient's PBL. The kit may include one or more oligonucleotides that are complementary to one or more transcripts identified herein as being associated with osteoarthritis, and also may include oligonucleotides related to necessary or meaningful assay controls. A kit for evaluating an individual for osteoarthritis may include pairs of oligonucleotides (e.g., 4, 6, 8, 10, 12, 14 or more oligonucleotides). The oligonucleotides may be designed to detect expression levels in accordance with any assay format, including but not limited to those described herein.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1

Increased Gene Expression of Certain Genes in Peripheral Blood Leukocytes is Associated with Increased Pain and Predicts Risk for Progression of Symptomatic Knee Osteoarthritis Patients, Materials and Methods Patients Three independent cohorts of patients were examined: two from NYUHJD (designated "Learning Cohort" and "NYUHJD Validation Cohort") and the "Duke Validation Cohort." Studies were approved by the Institutional Review Boards (IRB) of the NYU School of Medicine and Duke University, and all participants provided written informed consent prior to initiation of the studies.

NYUHJD Learning Cohort

PBL RNA from the initial 45 patients of the NYUHJD Learning Cohort with tibiofemoral OA and 25 non-OA healthy control volunteers was analyzed by Affymetrix microarray. Demographics, comorbidities, medications, number and location of joints affected (both by patient and physician report) were collected. Patients were diagnosed with knee OA by the referring physicians, according to the 1986 American College of Rheumatology classification and met clinical plus either radiographic or laboratory criteria for the diagnosis of idiopathic OA of the knee. Those with any other form of arthritis (including rheumatoid arthritis, spondyloarthritis, active crystal arthropathy); body mass index (BMI) ≥33; any disorder requiring the use of systemic corticosteroids within 1 week of screening; history of bilateral knee replacements; major co-morbidities including diabetes mellitus, non-cutaneous cancer within 5 years of screening, chronic hepatic or renal disease, chronic infectious disease, congestive heart failure; and hyaluronan and/or corticosteroid injection to the affected knee within 3 months of screening were excluded. Treatment of knee OA was left to the discretion of the treating physician. Healthy controls had no clinical signs or symptoms of any arthritis. Pain, functional status and quality of life were assessed with the Western Ontario and McMaster Osteoarthritis Index (WOMAC) (Bellamy et al., 1988, *J. Rheumatol.*, 15:1833-40), Short Form Health Survey (SF-36) (Ware & Sherbourne, 1992, *Med. Care*, 30:473-83), and Multidimensional Health Assessment Questionnaire (MDHAQ) (Pincus et al., 2005, *J. Rheumatol.*, 32:1432-9); within the MDHAQ are modules for the patient global assessment of their disease and for visual analog scale (VAS) pain assessment. From the NYUHJD learning cohort, PBLs were isolated and total RNA was extracted for microarray and QPCR analysis. PAXgene™ samples were also collected from non-OA participants.

The NYUHJD Validation Cohort

As part of an NIH-funded study, a separate cohort of 86 patients were followed for 24 months who met clinical symptomatic criteria [American College of Rheumatology (ACR)] (Altman et al., 1986, *Arthritis Rheum.*, 29:1039-49) and radiographic criteria [Kellgren-Lawrence (KL) grade≥1] (Kellgren & Lawrence, 1957, *Ann. Rheum. Dis.*, 16:494-502) for OA for at least one knee, and were >38 years old. Patients with histories of bilateral knee replacements, other forms of arthritis, cancer, or other chronic diseases beyond hypertension or hypercholesterolemia were excluded. All patients underwent bilateral standardized weight bearing fixed-flexion posteroanterior (PA) knee radiographs using the SynaFlexer™ X-ray positioning frame (Synarc). 41 age-matched healthy controls were also screened for the study, and among these, 20 subjects were recruited who had KL radiographic score <1 and no knee pain, of whom 12 were available for the analyses reported here. All patients were examined by an NYUHJD investigator every 6 months in this 24-month study. Radiographic assessments at baseline and 24 months include bilateral (signal and non-signal) KL determination, quantitative measurement of medial and lateral joint space width (JSW), medial and lateral JSN, osteophytes, medial tibial/lateral femoral subchondral sclerosis, and medial tibial attrition using the OARSI atlas by two musculoskeletal radiologists blinded to patient information. Kappas for inter-rater agreement were 0.85 and 0.77 for KL scores of the right and left knees, respectively, and >0.85 for most other radiographic outcome measures. Concordance correlation coefficients were >0.90 for JSW measurements. JSW was measured at the narrowest portion of the joint space via electronic calipers and a medical monitor and the average value between the two readers was used in the statistical analysis. Genomic DNA and RNA were collected from PBLs from each OA patient and non-OA control.

Duke Validation Cohort

A third independent population was selected from the Predict Osteoarthritis Progression (POP) study: a total of 159 participants (118 female, 41 male) were enrolled in the NIH-sponsored Strategies to Predict Osteoarthritis Progression (POP) study (N=56) (Kraus et al., 2009, *Ann. Rheum.*

Dis., 68:1673-9). Excluding patients with BMI this study provided data on 36 patients. The POP study patients were recruited from the Durham, NC area under a protocol approved by the Duke University IRB and in accordance with the policies of the Duke University Medical Center, and all patients gave written informed consent for studies of the genetics of OA.

Participants were recruited primarily through rheumatology and orthopaedic clinics and met the American College of Rheumatology (ACR) criteria for symptomatic OA of at least one knee. In addition, all participants met radiographic criteria for knee OA with a KL score of 1-3 in at least one knee. Exclusion criteria included the following: bilateral knee KL=4 scores; exposure to a corticosteroid (either parenteral or oral) within 3 months prior to the study evaluation; knee arthroscopic surgery within 6 months prior to the study evaluation; known history of avascular necrosis, inflammatory arthritis, Paget's disease, joint infection, periarticular fracture, neuropathic arthropathy, reactive arthritis, or gout involving the knee; and current anticoagulation. For gene expression studies by TaqMan QPCR analysis from the Duke patients, only PAXgene samples were utilized. Knee symptoms were ascertained by the NHANES I criterion (Davis et al., 1990, *Semin. Arthritis Rheum.*, 20(3 Suppl 1):34-41) of pain, aching or stiffness on most days of any one month in the last year; for subjects answering yes, symptoms were quantified as mild, moderate, or severe yielding a total score of 0-4 for each knee.

Sample Collection

Blood samples in the NYUHJD cohorts were collected in pyrogen-free heparinized tubes for isolation of PBLs and plasma, as well as serum collection tubes. PAXgene tubes were collected for RNA in all three cohorts. Blood was processed within 30 minutes of collection.

Isolation of PBLs

PBLs were isolated from venous blood of non-OA healthy control volunteers and OA patients, and purified by Ficoll-Hypaque density centrifugation as described (Boyam, 1968, *Scand. J. Clin. Lab. Invest.*, 21(Suppl 97):9-29).

Total RNA isolation and gene expression analysis

Total RNA from PBLs was isolated using Trizol and further purified using Qiagen RNeasy column. The RNA was quantified using spectrophotometry and integrity further checked on a 1% formaldehyde gel. Isolated total RNA was stored in aliquots at −70° C. Total RNA from PAXgene tubes was isolated using a PreAnalytiX blood RNA isolation kit according to the manufacturer's instructions (Qiagen Biosciences).

Real Time PCR (QPCR)

Total RNA (1 μg) was primed using oligo (dT)18 primers and cDNA synthesized using the Clontech cDNA synthesis kit following the manufacturer's directions (Clontech). Pre-designed TaqMan primer sets were purchased from Applied Biosystems. Real-time PCR reactions were run on the ABI Prism 7300 sequence detection system (Applied Biosystems) and relative expression levels calculated using the delta-delta comparative $C_T$ method (REF 23).

Labeling and hybridization of microarray

Five micrograms of total RNA was used for double-stranded cDNA synthesis using the Gibco BRL superscript choice system. For the first strand synthesis, a T7-(dT)24 oligomer was used. Double-stranded cDNA was purified further using phenol-chloroform and precipitated using ethanol, and suspended in 12 μl of DEPC. Eight μl of purified dscDNA were used for synthesis of biotin-labeled cRNA using an ENZO kit (Affymetrix). cRNA was purified using the Qiagen RNeasy kit, fragmented at 95° C. for 35 min for target preparation, and hybridized against Human U133A microarray (Affymetrix).

Normalization of Microarray Data

Raw expression data from array scans were pre-processed using the Affy package from Bioconductor, normalized using the RMA method of Irizarry et al. (Irizarry et al., 2003, *Biostatistics*, 4:249-64), and analyzed further using the R language for statistical computing (r-project.org on the World Wide Web). Genes with less than 70% reliable expression measurement ("present" call in Affymetrix) were filtered out, leaving 8700 genes for analysis.

Statistical Methods

Significance Analysis of Microarrays (SAM) was used to find genes that are differentially expressed between healthy controls and OA subjects and between subclasses of OA (Tusher et al., 2001, *Proc. Natl. Acad. Sci. USA*, 98:5116-21). The False Discovery Rate (FDR) method was used to control for multiple comparisons (Benjamini & Hochberg, 1995, J. Royal Stat. Society Series B, 57:289-300).

The "nearest shrunken centroid" approach implemented in the prediction analysis of microarrays method (PAM) of Tibshirani et al was used to construct a microarray biomarker of OA (Tibshirani et al., 2002, *Proc. Natl. Acad. Sci. USA*, 99:6567-72). Cross-validation was used to estimate its predictive power in discriminating between healthy control and OA samples.

The method of pre-validation was used to assess the significance of the microarray biomarker of OA while controlling for age, BMI and other demographic characteristics in a logistic regression model (Tibshirani & Efron, 2002, *Stat. Appl. Genet. Mol. Biol.*, 1:Article 1).

Box-Cox transformations were used to normalize variables prior to using statistical tests and regression models. All statistical analyses were performed using the R language for statistical computing and Bioconductor packages. Linear (logistic) regression methods were used to compare the groups ($OA^{IL-1}$, $OA^{th}$). Spearman's correlation coefficient r was used for different correlation analysis.

Results

Study Cohorts

As noted above, three independent cohorts of patients were examined: two from NYUHJD ("Learning Cohort" and "NYUHJD Validation Cohort") and the "Duke Validation Cohort." The strategy for identifying differentially expressed PBL genes in the NYUHJD Learning Cohort, and validating expression of those genes in the NYUHJD Validation and Duke Validation Cohorts, is outlined in FIG. 1.

NYUHJD Learning Cohort

45 OA patients and 25 non-OA healthy controls were recruited into the NYUHJD Learning Cohort. The OA patients of the NYUHJD Learning Cohort were significantly older (p <0.001) and had higher BMI than non-OA healthy controls (p=0.017). Approximately 30% of the subjects were males and 65% were white among the OA patients as well as the non-OA healthy controls. To address these differences in age and BMI, a sub-cohort (designated the Matched Sub-cohort) of 19 OA patients and 17 healthy controls were selected from NYUHJD Learning Cohort, frequency-matched on age, gender ethnicity, and BMI for further analysis.

PBL Gene Expression Profile as a Diagnostic Combinatorial Biomarker: Pre-Validated Microarray Predictor Using the nearest shrunken centroid approach, a microarray combinatorial biomarker diagnostic of OA was constructed based on the NYUHJD Learning Cohort microarray data. This analysis was done based on the entire NYUHJD Learning Cohort and repeated based on the matched sub-cohort. A logistic regression model was fitted using the microarray biomarker alone and in combination with BMI, age and ethnicity as independent variables. To reduce bias associated with re-use of the data, the presence of BMI, age and gender were used with the method of pre-validation when assessing the significance of the microarray predictor (Tibsharani & Efron, supra). The pre-validated microarray predictor was significant when alone (p=0.0002) and while controlling for the subject characteristics (p=0.0017). Significant predictors included the differential gene expression profile microarray [odds ratio (OR) 8.51, 95% confidence interval (CI) 2.03-35.7], age (OR 1.10, 95% CI 1.02-1.19) and BMI (OR 1.23, 95% CI 1.02-1.49).

Significant Genes

Using the NYUHJD Learning Cohort, 332 upregulated genes and 193 downregulated genes were identified in OA using a FDR of 5% and with at least a 1.25-fold change. Using the matched sub-cohort, 828 upregulated genes and 448 downregulated genes were identified in OA using the same criteria. Seventy-three percent of the upregulated genes and 62% of the down-regulated genes identified using data on all subjects were also found to be significant, based on the matched sub-cohort data. Among the most significant genes were junB, CDC42, Granulin, MMP-9 and cyclin D2. Using the method of cross-validation, it was estimated that this gene expression pattern has a sensitivity of about 89% and a specificity of about 76% for an OA diagnosis (see Tables 5 and 6).

PBL Inflammatory Gene Expression Identifies OA Subclasses

Figure 2A:
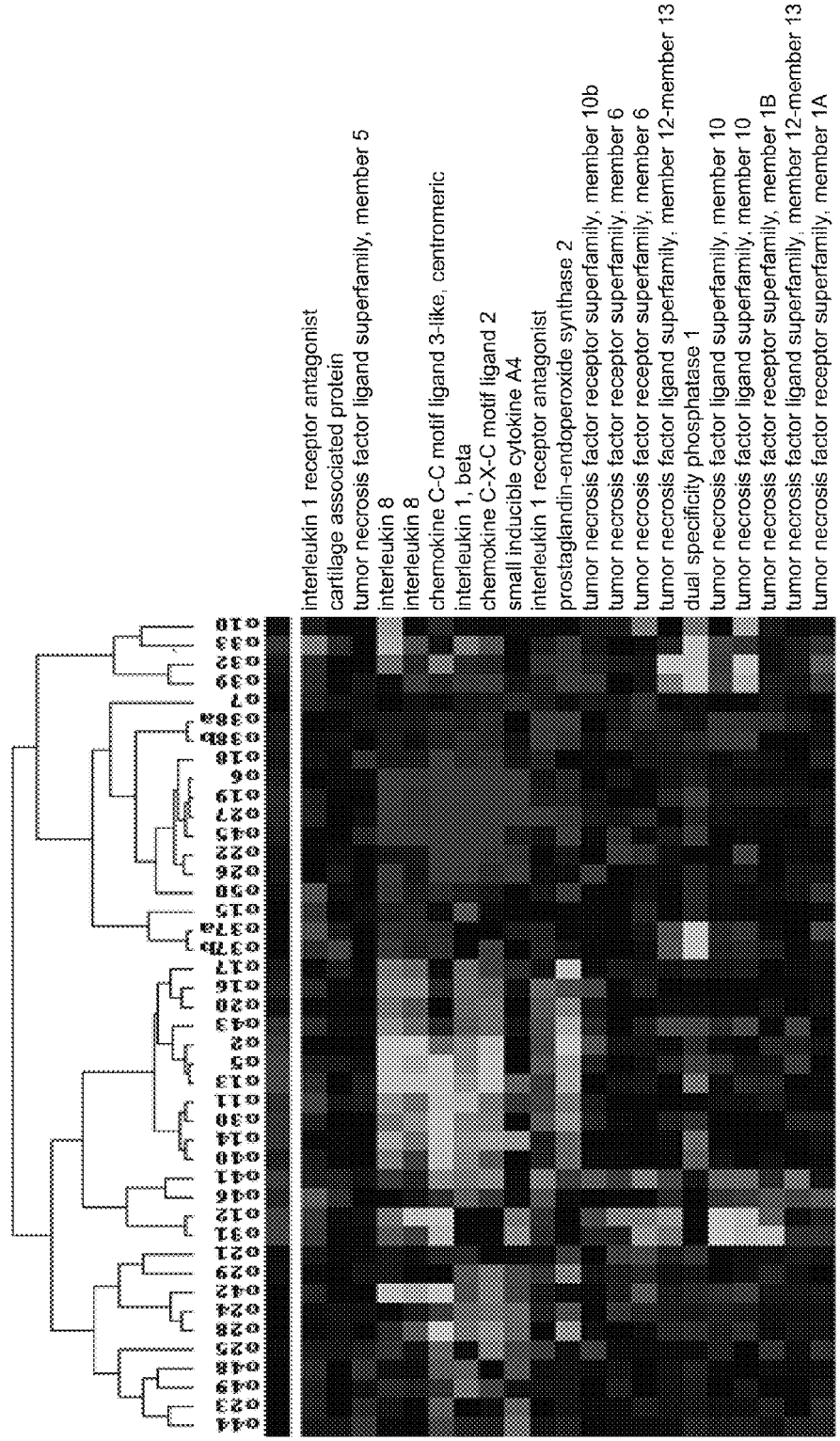
FIG. 2A shows that hierarchical clustering of samples identified two subclasses of OA based on gene expression of 21 selected cytokines: cytokine overexpressors ($OA^{IL-1}$) and cytokine underexpressors ($OA^{nl}$). The cytokines are IL-1β, IL-8, COX-2 and the chemokines are GRO2, cytokine A3 (MIP-1α) and cytokine A4 (MIP-1β).

Given the role that inflammation in joint tissues has been shown to play, it was next determined whether there was evidence that PBLs in selected patients were "activated," reflecting exposure to inflammatory stimuli as these cells traversed diseased synovium and bone. Therefore, to identify subclasses of OA, the NYUHJD Learning Cohort OA samples were randomly divided into a separate training set (23 samples) and test set (22 samples+3 replicates). The samples had been pre-stratified to ensure that the two sets were frequency matched on sex, ethnicity and BMI. In the training set, complete-linkage hierarchical clustering was used to identify subclasses of OA based on the expression of 21 pre-selected cytokine genes (see Table 1) and TreeView to visualize the results (Eisen et al., 1998, *Proc. Natl. Acad. Sci. USA*, 95:14863-8). Of the 21 pre-selected inflammatory genes, 7 of these genes stratified OA into two subclasses as shown in FIG. 2A.

TABLE 1

Cytokine Genes Used To Define OA Subclasses.

| Gene ID | Gene name |
|---|---|
| 39402_at | interleukin 1, beta |
| 211506_s_at | interleukin 8 |
| 204748_at | prostaglandin-endoperoxide synthase 2 (COX-2) |
| 202859_x_at | interleukin 8 |
| 201044_x_at | dual specificity phosphatase 1 |
| 212657_s_at | interleukin 1 receptor antagonist |
| 212659_s_at | interleukin 1 receptor antagonist |
| 209774_x_at | chemokine (C—X—C motif) ligand 2 |
| 205114_s_at | chemokine (C-C motif) ligand 3-like, centromeric |
| 204103_at | CCL4 (MIP-1 beta) |
| 202687_s_at | tumor necrosis factor (ligand) superfamily, member 10 |
| 202688_at | tumor necrosis factor (ligand) superfamily, member 10 |

TABLE 1-continued

Cytokine Genes Used To Define OA Subclasses.

| Gene ID | Gene name |
|---|---|
| 203508_at | tumor necrosis factor receptor superfamily, member 1B |
| 204780_s_at | tumor necrosis factor receptor superfamily, member 6 |
| 204781_s_at | tumor necrosis factor receptor superfamily, member 6 |
| 207643_s_at | tumor necrosis factor receptor superfamily, member 1A |
| 207892_at | tumor necrosis factor (ligand) superfamily, member 5 |
| 209295_at | tumor necrosis factor receptor superfamily, member 10b |
| 209499_x_at | tumor necrosis factor (ligand) superfamily, member 12-member 13 |
| 209500_x_at | tumor necrosis factor (ligand) superfamily, member 12-member 13 |
| 201380_at | cartilage associated protein |

Figure 2B:
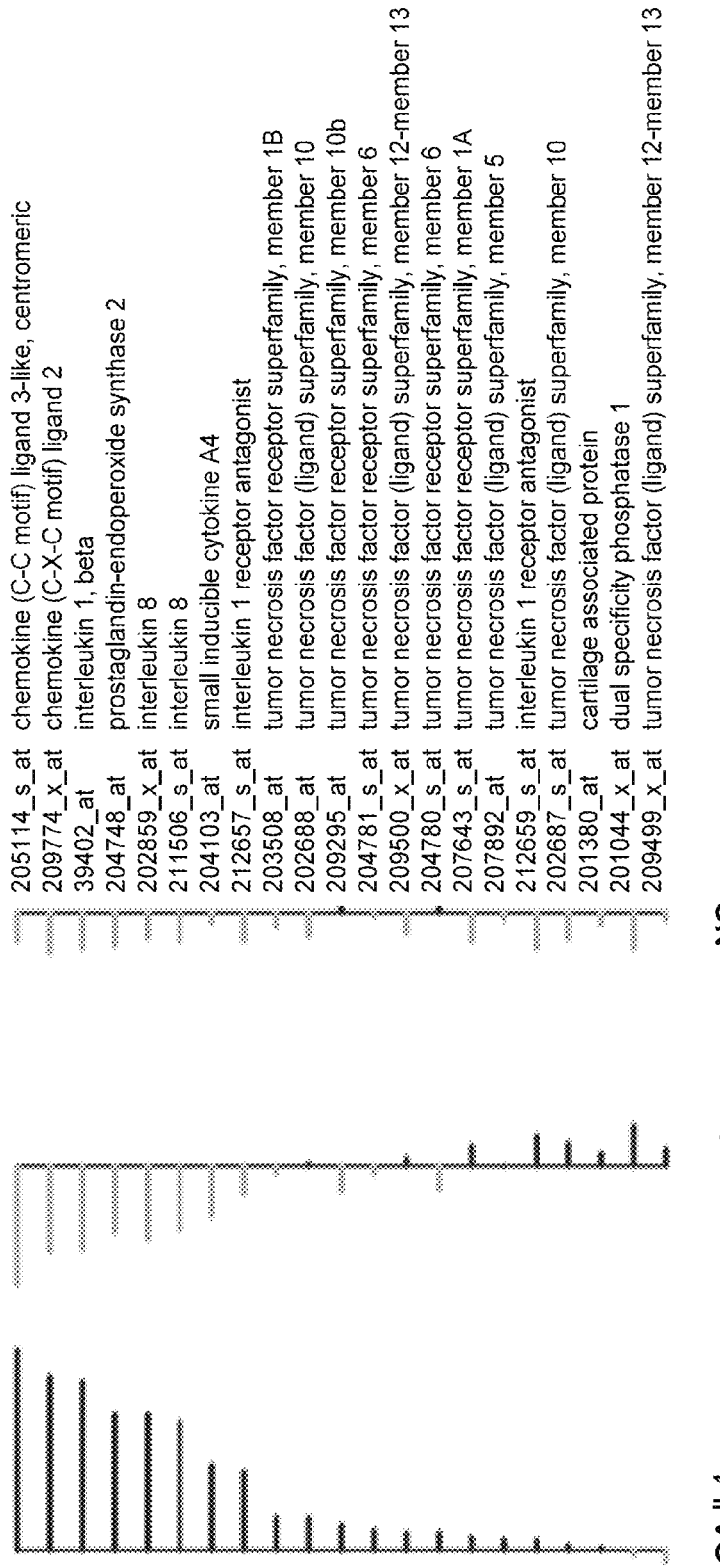
FIG. 2B shows the centroids of OA subclasses. The horizontal bars represent the average gene expression for each of the three classes: $OA^{IL-1}$, $OA^{nl}$ and non-OA controls. The black bars indicate positive average expression while the grey bars indicate negative average expression.

Two subclasses of OA were identified in the training set: cytokine overexpressors ($OA^{IL-1}$) and cytokine underexpressors ($OA^{IL-1}$). $OA^{IL-1}$ class had elevated levels of IL-1β (up 6.56-fold), IL-8 (up 2-fold), COX-2 (up 2.75-fold), and chemokines GRO2 (up 5.37-fold), macrophage inflammatory protein-1α (MIP-1α) (up 6-fold) and MIP-1β (up 2.75-fold). Based on the gene expression of the 21 cytokines, the centroids C1 and C2 of OA classes in the training set was computed and each OA test sample was labeled as $OA^{IL-1}$ or $OA^{nl}$ according to whether it was most correlated with C1 or C2. Therefore, OA classes were defined using cluster analysis based solely on the expression of the 21 cytokine genes. The centroids of the two classes of OA are depicted in FIG. 2B.

Cross-Validated Gene Expression (Excluding 21 Cytokine Genes) Predictor of OA Classes Using the method of nearest shrunken centroids, a 10-fold cross-validated predictor was constructed of these cluster-defined subclasses of OA based on the training set and excluding the 21 cluster-defining inflammatory genes in order to find whether other genes or probe sets can stratify subsets of OA patients. The resulting microarray predictor of OA subclasses consisted of eight genes including cytokine genes such as IL-1β (a different probe set) and TNF inducible proteins (see Table 7). The performance of the resulting 8-gene predictor of OA subclass was evaluated using the test set. The training, cross-validated and test set error of this gene expression predictor of OA subclass was estimated to be over 96%.

Analysis of Differentially Expressed Cytokines by Real Time RT-PCR

Figure 3A:
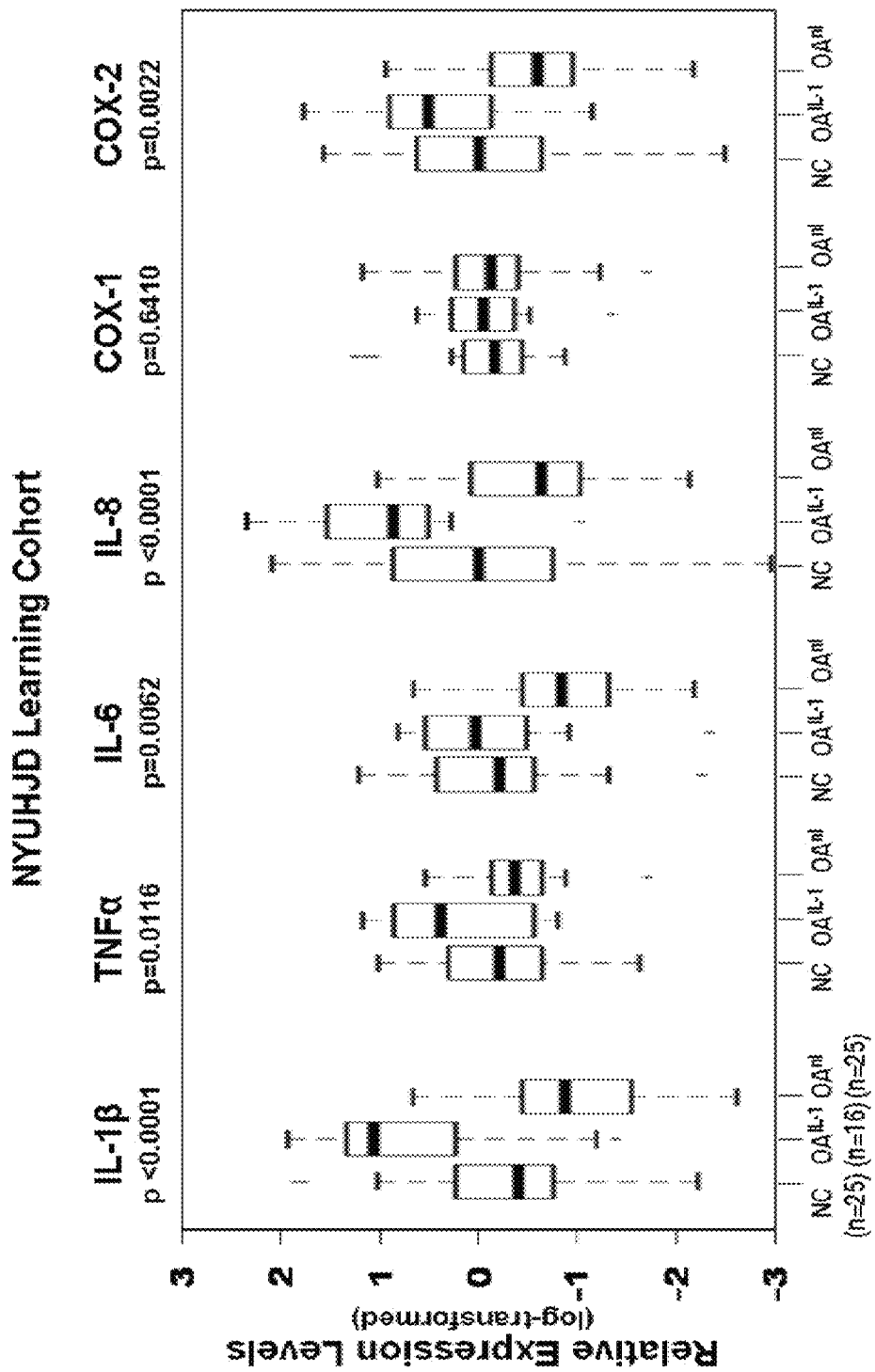
FIG. 3A is a graphical representation of real-time PCR analysis of expression of inflammatory genes (IL-1β, TNFα, IL-8, IL-6, COX-1 and COX-2) in OA PBLs in the NYUHJD learning cohort. The data show that five of these genes are differentially over-expressed in the $OA^{IL-1}$ group as compared to non-OA normal controls and $OA^{nl}$.

TaqMan real-time QPCR was performed to confirm the findings based on microarrays. The pre-designed primers were purchased from Applied Biosystems. In this study, expression of three different house-keeping genes was analyzed, actin (act), glycerolaldehyde-3 phosphate dehydrogenase (GAPDH) and ribosomal protein large PO (RPLPO). Among the three, only GAPDH did not show any significant difference between the non-OA control and OA group. The "inflammatory" genes IL-1β, TNFα, IL-6, IL-8, COX-1 and COX-2 also were analyzed. The relative fold change of each gene was calculated using the delta-delta comparative $C_T$ method (Livak & Schmittgen, 2001, *Methods*, 25:402-8). As observed by microarray data, significantly elevated levels of IL-1β, TNFα, IL-6, IL-8 and COX-2 expression were observed in the $OA^{IL-1}$ as compared to the $OA^{nl}$ subclass (FIG. 3A). Additionally, IL-1β and IL-6 levels were significantly associated with pain in the linear regression model while controlling the effects of age, BMI, gender and ethnicity (adjusted p=0.02 and 0.04, respectively, FIG. 3D). Elevated Inflammatory Gene Expression in OA PBLs is Confirmed in Two Independent Cohorts To further confirm the elevated levels of both genes as diagnostic biomarkers, a specific OA subset, two different additional independent cohorts of OA patients recruited from both Duke University and NYUHJD were used: 1) The Duke Validation Cohort consisted of 36 OA patients and no controls; the Duke OA patients had higher mean BMI than the patients in the other cohorts (Table 2); and 2) The NYUHJD Validation Cohort consisted of 86 OA patients and 12 non-OA controls (Table 2). As noted, $OAz^{IL-1}$ and $OA^{nl}$ subclasses in the validation cohorts was defined based on the samples IL-1 expression using the 90% quantile method.

model while controlling for age, BMI, gender and ethnicity (adjusted p=0.0009, 0.01 and 0.02 for pain VAS, WOMAC total and WOMAC pain, respectively) in the NYUHJD validation cohort.

TABLE 3

Baseline WOMAC and pain visual analog scale (VAS) scores in OA patients with increased ($OA^{IL-1}$) versus normal ($OA^{nl}$) IL-1β expression (NYUHJD Validation Cohort).

| Pain Score | Mean (±SD) | | p-value[1] |
|---|---|---|---|
| | $OA^{IL-1}$ (n = 33) | $OA^{nl}$ (n = 53) | |
| WOMAC sum pain | 52.16 (23.67) | 37.05 (19.81) | 0.0034 |
| sum stiffness | 57.28 (23.66) | 40.94 (22.14) | 0.0023 |

TABLE 2

Comparison of OA subclasses with respect to various demographic and clinical characteristics.

| | | NYUHJD Learning Cohort | | | Duke Validation Cohort | | NYUHJD Validation Cohort | | |
|---|---|---|---|---|---|---|---|---|---|
| | | $OA^{IL-1}$ (n = 16) | $OA^{nl}$ (n = 25) | NC (n = 25) | $OA^{IL-1}$ (n = 8) | $OA^{nl}$ (n = 28) | $OA^{IL-1}$ (n = 33) | $OA^{nl}$ (n = 53) | NC (n = 12) |
| Gender | M | 2 (12%) | 8 (32%) | 7 (28%) | 1 (17%) | 7 (18%) | 11 (33.3%) | 24 (45.2%) | 8 (66.7%) |
| | F | 14 (88%) | 17 (68%) | 18 (72%) | 7 (83%) | 21 (82%) | 22 (66.7%) | 29 (55%) | 4 (33.3%) |
| Ethnicity | H | 3 (19%) | 7 (28%) | 5 (20%) | 1 (17%) | 0 (0%) | 6 (18.2%) | 6 (11.%) | 0 (0%) |
| | NH | 13 (81%) | 18 (82%) | 20 (80%) | 7 (83%) | 28 (100%) | 27 (81.2%) | 47 (88%) | 12 (100%) |
| Age | Mean (SD) | 64.0 (11.4) | 67.6 (10.0) | 54.1 (9.4) | 55.4 (13.7) | 64.4 (12.3) | 59.21 (8.96) | 63.2 (9.2) | 59.67 (9.2) |
| BMI | | 25.4[1] (3.2) | 27.7[1] (3.3) | 24.5 (3.5) | 29.7 (2.25) | 27.6 (3.15) | 27.1 (3.45) | 26.5 (3.5) | 25.4 (3.7) |
| Joints affected | | 3.6 (1.4) | 3.8 (2.0) | NA | NA | NA | NA | NA | NA |

Figures 3B, 3C:
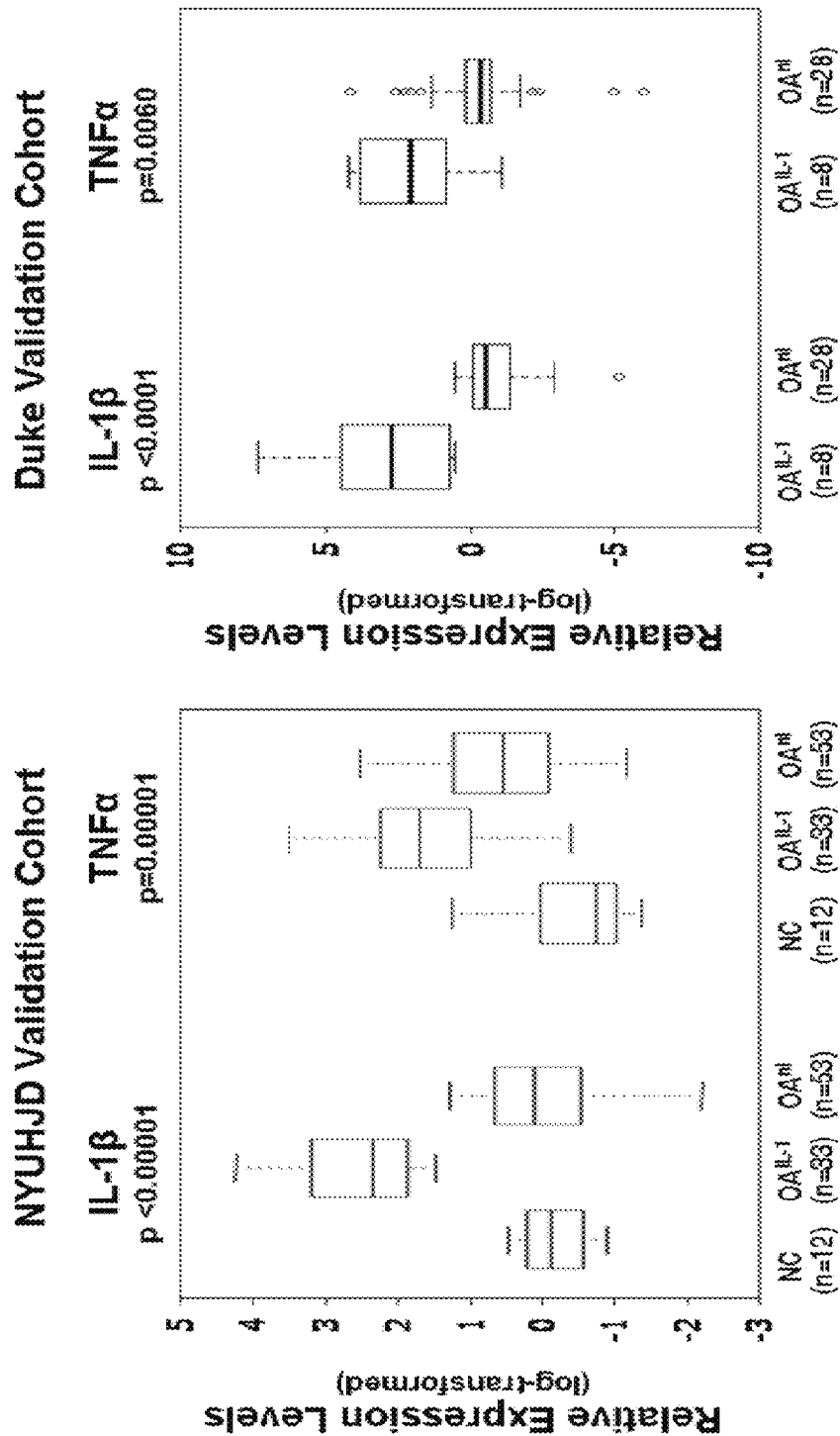
FIGS. 3B-C demonstrate the distributions of IL-1 and TNF expression levels by group in validation cohorts and correlation with pain score. Real-time PCR analysis: relative fold changes of IL-1 expression in (B) the NYUHJD validation cohort and (C) Duke validation cohort by group. These data show that IL-1 gene is differentially overexpressed in the $OA^{IL-1}$ group as compared to non-OA controls (NC) and $OA^{IL-1}$.
Figure 3D:
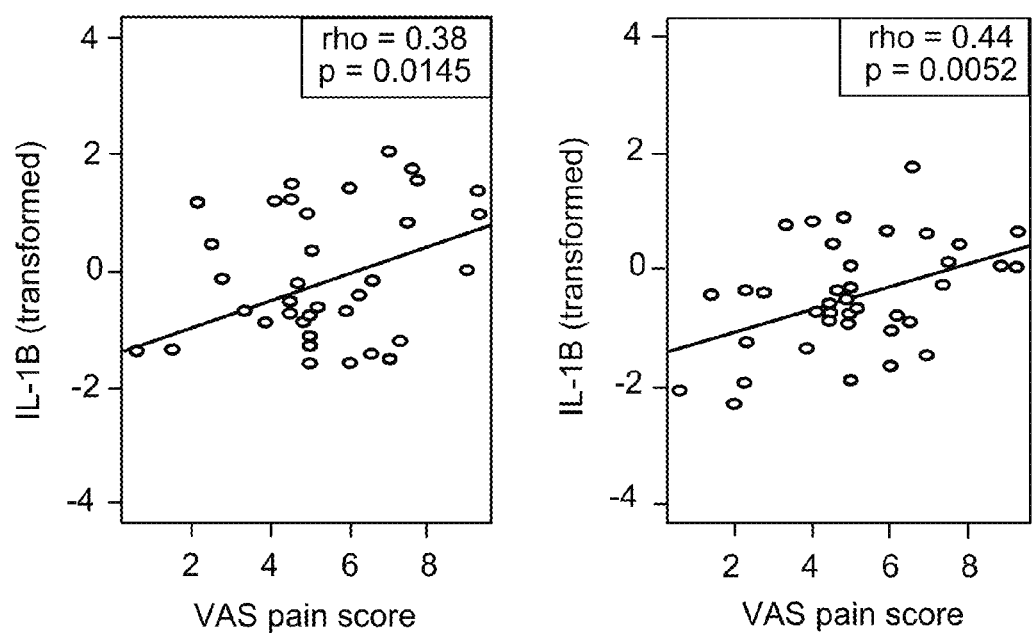
FIG. 3D are graphs showing the association of inflammatory gene expression levels in OA PBL with pain score. Relative expression levels of inflammatory genes quantitated by QPCR in OA PBLs were correlated with pain assessment scores in the linear regression model while controlling for age, BMI, gender and ethnicity. Among the inflammatory genes, only IL-1β and IL-6 levels were significantly associated with pain in the linear regression model while controlling the effects of age, BMI, gender and ethnicity (adjusted p=0.02 and 0.04, respectively). Box-Cox transformations were applied to normalize variables prior to regression modeling.

[1]Difference statistically significant (p = 0.04, p = 0.0035 in females) using two-sided rank-sum test As observed in NYUHJD Learning Cohort, elevated expression of IL-1β, and TNFα was confirmed in both the NYUHJD and DUKE validation cohorts (FIGS. 3B-C). For the NYUHJD Validation Cohorts, the OA subjects were defined as cytokine overexpressors ($OA^{IL-1}$ class) if they had an elevated expression (at least 2-fold) of IL-1β. Some of these characteristics of the $OA^{IL-1}$ and $OA^{nl}$ subclasses of the NYUHJD learning cohort were also confirmed in the NYUHJD validation cohorts. Specifically, the pain assessment scores were significantly higher in the $OA^{IL-1}$ subclass than in $OA^{nl}$ class by all three measures (WOMAC pain, p=0.0077; WOMAC total, p=0.0119; pain VAS, p=0.0012) in the NYUHJD validation cohort (Table 3). Additionally, IL-1 levels were significantly associated with pain assessment scores by all three measures in the linear regression

TABLE 3-continued

Baseline WOMAC and pain visual analog scale (VAS) scores in OA patients with increased ($OA^{IL-1}$) versus normal ($OA^{nl}$) IL-1β expression (NYUHJD Validation Cohort).

| Pain Score | Mean (±SD) | | p-value[1] |
|---|---|---|---|
| | $OA^{IL-1}$ (n = 33) | $OA^{nl}$ (n = 53) | |
| sum physical function | 52.33 (22.36) | 34.19 (20.04) | 0.0003 |
| Total score | 161.78 (64.01) | 112.18 (55.84) | 0.0004 |
| Pain VAS | 61.80 (25.80) | 42.77 (28.17) | 0.0069 |

[1]Linear regression adjusted for BMI, gender, race and age

The OA$^{IL-1}$ Subset is at Increased Risk for Radiographic Progression

Eighty-six patients in the NYUHJD Validation Cohort completed a 24-month study of radiographic progression. Comparing standardized fixed-flexion radiographs read independently by two radiologist (LR, JB), changes in JSW (both in millimeters and as >30% change from baseline) and KL scores was determined between visit 0 and 24 months. For KL scores, a change in one grade was considered to represent progression. OA$^{IL-1}$ patients exhibited greater JSN at 24 months than the OA$^{nl}$ group (0.76 vs 0.15 mm, p<0.02) (Table 4A). Since the mean JSW at baseline between OA$^{IL-1}$ (3.8±1.7 mm) and OA$^{nl}$ (2.1±2.1 mm) groups was different, those OA patients who had ≥3 mm baseline JSW were analyzed separately. In this sub-analysis (Table 4B), the JSN at baseline remained higher in the OA$^{IL-1}$ group compared to OA$^{nl}$ group, and OA$^{IL-1}$ patients exhibited greater JSN at 24 months than the OA$^{nl}$ group (0.89 vs 0.38 mm, p=0.0507). Logistic regression analysis adjusted for BMI, age and gender also showed that the OA$^{IL-1}$ group demonstrated increased progression as assessed by decrease in JSW (i.e., JSN) >30%, which was observed in 19 of 86 patients (Table 4C; OR=3.2, p<0.03). Thus, using percent change in JSW (JSN>30%), a top quartile of "fast progressors" were identified at baseline by increased PBL expression of IL-1β. Additionally, using the same logistic regression model, the change of KL score in the OA$^{IL-1}$ group was significantly greater (p<0.004) compared to the OA$^{nl}$ group over 24 months. After controlling for BMI, age and gender, OA$^{IL-1}$ also exhibited clinical features that differed from OA$^{nl}$ patients, with higher WOMAC pain, decreased physical function and higher VAS pain scores (p=0.0069) (Table 3).

TABLE 4

Baseline and 24 month follow up

Table 4A: JSW (mm) signal knee, medial

| | Mean (standard deviation) | | |
|---|---|---|---|
| | OA$^{IL-1}$ (n = 33) | OA$^{nl}$ (n = 53) | p-value[1] |
| Baseline | 3.87 (1.71) | 2.14 (2.15) | 0.0005 |
| 24 months | 3.10 (1.79) | 2.01(2.10) | 0.0259 |
| Change (JSN) | 0.77 (0.95) | 0.15 (1.23) | 0.0208 |

Table 4B: JSW signal in patients with baseline JSW ≥3 mm

| | Mean (standard deviation) | | |
|---|---|---|---|
| | OA$^{IL-1}$ (n = 25) | OA$^{nl}$ (n = 28) | p-value[1] |
| Baseline | 4.67 (0.28) | 4.25 (0.19) | 0.142 |
| 24 months | 3.78 (0.35) | 3.86 (0.24) | 0.8203 |
| Change (JSN) | 0.89 (0.26) | 0.38 (0.18) | 0.0507 |

Table 4C: JSN (>30%) OA$^{IL-1}$ vs. OA$^{nl}$

| | Odds ratio [95% CI] | p-value[2] |
|---|---|---|
| Signal knee | 3.17 [1.16-8.66] | 0.0247 |

[1]Linear regression adjusted for BMI, gender, race and age
[2]Logistic regression adjusted for BMI, gender, race and age PBL Overexpression of TNFα also Predicts OA Progression An analysis of the 86 "completer" patients also revealed that patients who are high expressors of IL-1β (OA$^{IL-1}$) exhibit increased PBL gene expression of TNFα (OA$^{TNFα}$) (significant positive correlation r=0.78, p<0.001). Therefore, patients were also stratified based on PBL TNFα expression (QPCR) into OA$^{TNFα}$ and OA$^{nl(TNF)}$, whose TNFα expression was comparable to controls. Similar to the OA$^{IL-1}$ group, the OA$^{TNFα}$ group demonstrated increased risk of progression in the signal knee compared to OA$^{nl(TNF)}$ group, as assessed by JSN greater than 30% (OR=8.9; 95% CI 2.57-30.81; p<0.0005).

TABLE 5

Significantly upregulated genes in OA

| Gene ID | Gene Name | Fold Change | FDR (%) |
|---|---|---|---|
| 209286_at | Cdc42 effector protein 3 | 1.792233 | 0 |
| 211133_x_at | Leukocyte receptor, subfamily B, member 3 | 1.532934 | 0 |
| 205211_s_at | Ras inhibitor | 1.577013 | 0 |
| 221507_at | Karyopherin beta 2b, transportin | 1.576684 | 0 |
| 217763_s_at | RAB31, member RAS oncogene family | 1.734823 | 0 |
| 201369_s_at | Zinc finger protein 36, C3H type-like 2 | 2.177888 | 0 |
| 207730_x_at | hypothetical protein FLJ20700 | 2.122161 | 0 |
| 215067_x_at | NA | 1.786506 | 0 |
| 206792_x_at | Phosphodiesterase 4C, cAMP-specific | 1.862949 | 0 |
| 211600_at | Protein tyrosine phosphatase, receptor type, O | 1.655395 | 0 |
| 204771_s_at | Transcription termination factor, RNA polymerase I | 1.611597 | 0 |
| 211452_x_at | Leucine rich repeat (in FLII) interacting protein 1 | 1.528075 | 0 |
| 208961_s_at | Core promoter element binding protein | 1.588829 | 0 |
| 216187_x_at | NA | 1.999088 | 0 |
| 205212_s_at | Centaurin, beta 1 | 1.65822 | 0 |
| 35265_at | Fragile X mental retardation, autosomal homolog 2 | 1.543233 | 0 |
| 201473_at | Jun B proto-oncogene | 1.729234 | 0 |
| 203936_s_at | Matrix metalloproteinase 9 | 1.554202 | 0 |
| 201536_at | dual specificity phosphatase 3 | 1.507242 | 0 |
| 211284_s_at | granulin | 1.597269 | 0 |
| 220071_x_at | hypothetical protein FLJ10460 | 1.901346 | 0 |
| 221753_at | KIAA1298 protein | 1.552561 | 0 |
| 208141_s_at | hypothetical protein MGC4293 | 1.644862 | 0 |
| 220113_x_at | similar to DNA-directed RNA polymerase I | 1.721127 | 0 |
| 208246_x_at | hypothetical protein FLJ20006 | 1.880997 | 0 |
| 210778_s_at | Mad4 homolog | 1.676753 | 0 |
| 207105_s_at | phosphoinositide-3-kinase | 1.544 | 0 |
| 212086_x_at | lamin A/C | 1.605936 | 0 |
| 215978_x_at | NA | 1.96545 | 0 |
| 215404_x_at | hypothetical protein FLJ14326 | 1.756882 | 0 |
| 213642_at | ribosomal protein L27 | 2.135468 | 0 |
| 222244_s_at | hypothetical protein FLJ20618 | 1.508162 | 0 |
| 215604_x_at | NA | 1.68866 | 0 |
| 217579_x_at | NA | 1.58921 | 0 |
| 214041_x_at | ribosomal protein L37a | 2.397426 | 0 |
| 215588_x_at | NA | 1.698163 | 0 |
| 200874_s_at | nucleolar protein (KKE/D repeat) | 1.580683 | 0 |
| 214715_x_at | KRAB zinc finger protein KR18 | 1.810311 | 0 |
| 214182_at | ADP-ribosylation factor 6 | 2.059147 | 0 |
| 217679_x_at | NA | 2.101391 | 0 |
| 205312_s_at | spleen focus forming virus | 1.989689 | 0 |
| 215373_x_at | hypothetical protein FLJ12151 | 1.777239 | 0 |
| 218155_x_at | hypothetical protein FLJ10534 | 1.816128 | 0 |
| 205367_at | adaptor protein | 1.501157 | 0 |
| 213048_s_at | SET translocation (ML-associated) | 2.045591 | 0 |
| 212368_at | KIAA0530 protein | 1.634256 | 0 |
| 212520_s_at | chromatin regulator, subfamily a, member 4 | 1.518527 | 0 |
| 208137_x_at | hypothetical protein MGC5384 | 1.683952 | 0 |
| 211040_x_at | G-2 and S-phase expressed 1 | 1.525785 | 0 |
| 215628_x_at | NA | 1.643881 | 0 |

TABLE 5-continued

Significantly upregulated genes in OA

| Gene ID | Gene Name | Fold Change | FDR (%) |
|---|---|---|---|
| 204403_x_at | KIAA0738 gene product | 1.590101 | 0 |
| 215383_x_at | NA | 1.542431 | 0 |
| 214594_x_at | ATPase, Class I, type 8B, member 1 | 1.925712 | 0 |
| 208868_s_at | GABA(A) receptor-associated protein like 1 | 1.522878 | 0 |
| 213619_at | heterogeneous nuclear ribonucleoprotein H1 (H) | 1.731203 | 0 |
| 220252_at | hypothetical protein FLJ11577 | 1.60942 | 0 |
| 202205_at | vasodilator-stimulated phosphoprotein | 1.76824 | 0 |
| 215063_x_at | NA | 1.541363 | 0 |
| 215179_x_at | NA | 1.648163 | 0 |
| 206565_x_at | SMA3 | 2.035635 | 0 |
| 219392_x_at | hypothetical protein FLJ11029 | 1.649219 | 0 |
| 217446_x_at | NA | 1.663199 | 0 |
| 206207_at | Charot-Leyden crystal protein | 1.848486 | 0 |
| 217610_at | NA | 1.615029 | 0 |
| 212952_at | calreticulin | 1.825903 | 0 |
| 205099_s_at | chemokine (C-C motif) receptor 1 | 1.582214 | 0 |
| 217713_x_at | NA | 1.565506 | 0 |
| 200630_x_at | SET translocation (myeloid leukemia-associated) | 1.844666 | 0 |
| 203523_at | lymphocyte-specific protein 1 | 1.525218 | 0 |
| 215600_at | NA | 1.643765 | 0 |
| 209710_at | GATA binding protein 2 | 1.565236 | 0 |
| 215208_x_at | NA | 1.543211 | 0 |
| 219290_x_at | dual adaptor of phosphotyrosine and 3-phosphoinositides | 1.51031 | 0 |
| 220796_x_at | hypothetical protein FLJ14251 | 1.698134 | 0 |
| 216176_at | NA | 1.519981 | 0 |
| 201353_s_at | bromodomain adjacent to zinc finger domain, 2A | 1.628074 | 0 |
| 212291_at | KIAA0630 protein | 1.894984 | 0 |
| 205370_x_at | dihydrolipoamide branched chain transacylase | 1.583879 | 0 |
| 209964_s_at | spinocerebellar ataxia 7 | 1.535959 | 0 |
| 211794_at | FYN binding protein | 1.571693 | 0 |
| 209880_s_at | selectin P ligand | 1.528431 | 0 |
| 211734_s_at | Fc fragment of IgE, receptor, high affinity I | 1.683284 | 0 |
| 210679_x_at | B-cell CLL/lymphoma 7A | 1.676555 | 0 |
| 222104_x_at | general transcription factor IIH, polypeptide 3 | 1.634487 | 0 |
| 214707_x_at | KIAA0328 protein | 1.594532 | 0 |
| 210136_at | myelin basic protein | 1.526484 | 0 |
| 211454_x_at | origin recognition complex, subunit 6 | 1.685494 | 0 |
| 214316_x_at | calreticulin | 1.571818 | 0 |
| 201502_s_at | nuclear factor of kappa polypeptide gene enhancer | 1.853858 | 0 |
| 203085_s_at | transforming growth factor, beta 1 | 1.619631 | 0 |
| 221473_x_at | tumor differentially expressed 1 | 1.651826 | 0 |
| 214902_at | NA | 1.524789 | 0 |
| 216858_x_at | NA | 1.703859 | 0 |
| 212099_at | ras homolog gene family, member B | 2.157175 | 0 |
| 203411_at | lamin A/C | 1.502834 | 0.417324 |
| 207365_at | KIAA0570 gene product | 1.553988 | 0.417324 |
| 210231_x_at | SET translocation (ML-associated) | 1.75472 | 0.417324 |
| 202191_s_at | growth arrest-specific 7 | 1.596873 | 0.417324 |
| 215078_at | NA | 1.621117 | 0.417324 |
| 208960_s_at | core promoter element binding protein | 1.544492 | 0.417324 |
| 208082_s_at | makorin, ring finger protein, 4 | 1.522376 | 0.417324 |
| 206655_s_at | glycoprotein Ib (platelet), beta polypeptide | 1.648082 | 0.417324 |
| 204786_s_at | interferon receptor 2 | 1.533576 | 0.417324 |
| 204713_s_at | coagulation factor V | 1.513809 | 0.417324 |
| 210686_x_at | NA | 1.532889 | 0.784444 |
| 205967_at | H4 histone family, member G | 1.503579 | 0.784444 |
| 200808_s_at | zyxin | 1.749096 | 0.784444 |
| 222303_at | NA | 1.640311 | 0.784444 |
| 214257_s_at | NA | 1.669045 | 0.784444 |
| 213746_s_at | filamin A, alpha (actin binding protein 280) | 1.522938 | 0.784444 |
| 202014_at | protein phosphatase 1, subunit 15A | 1.660389 | 0.784444 |
| 215123_at | NA | 1.837685 | 0.784444 |
| 204081_at | neurogranin (protein kinase C substrate, RC3) | 1.540214 | 0.784444 |
| 211769_x_at | tumor differentially expressed 1 | 1.541098 | 1.102089 |
| 215043_s_at | SMA5 | 1.876365 | 1.102089 |
| 200800_s_at | heat shock 70 kD protein 1A | 1.518232 | 1.102089 |
| 213979_s_at | C-terminal binding protein 1 | 1.736157 | 1.102089 |
| 213757_at | eukaryotic translation initiation factor 5A | 1.651862 | 1.439049 |
| 215175_at | KIAA0995 protein | 1.515357 | 1.704756 |
| 205114_s_at | small inducible cytokine A3 | 1.951794 | 1.704756 |
| 203239_s_at | CCR4-NOT transcription complex, subunit 3 | 1.574555 | 2.311131 |
| 221943_x_at | ribosomal protein L38 | 1.916548 | 2.311131 |
| 37028_at | protein phosphatase 1, subunit 15A | 1.532029 | 2.311131 |
| 200852_x_at | guanine nucleotide binding protein | 1.502994 | 2.311131 |
| 201631_s_at | immediate early response 3 | 1.551771 | 2.62468 |
| 208727_s_at | cell division cycle 42 | 1.774784 | 2.62468 |
| 212044_s_at | ribosomal protein L27a | 1.643742 | 2.862742 |
| 216983_s_at | NA | 1.531637 | 2.862742 |
| 219599_s_at | hypothetical protein PRO1843 | 2.029631 | 2.862742 |
| 203254_s_at | talin 1 | 1.513678 | 3.142501 |
| 201367_s_at | zinc finger protein 36, C3H type-like 2 | 1.866414 | 3.142501 |
| 210172_at | NA | 1.588887 | 3.436052 |
| 202028_s_at | ribosomal protein L38 | 1.750071 | 3.989128 |
| 205033_s_at | defensin, alpha 1, myeloid-related sequence | 1.846809 | 4.270862 |
| 211317_s_at | CASP8 and FADD-like apoptosis regulator | 1.500032 | 4.523022 |
| 210858_x_at | ataxia telangiectasia mutated | 1.576574 | 4.523022 |

TABLE 6

Significantly downregulated genes in OA

| Gene ID | Gene Name | Fold Change | FDR (%) |
|---|---|---|---|
| 213009_s_at | tripartite motif-containing 37 | 0.63842 | 0 |
| 210346_s_at | NA | 0.66458 | 0 |
| 218313_s_at | polypeptide transferase 7 | 0.65304 | 0 |
| 202271_at | KIAA0483 protein | 0.65087 | 0 |
| 221931_s_at | sec13-like protein | 0.64607 | 0 |
| 202979_s_at | HCF-binding transcription factor Zhangfei | 0.61396 | 0 |
| 210356_x_at | membrane-spanning 4-domains | 0.52081 | 0 |
| 222150_s_at | hypothetical protein | 0.66339 | 0 |
| 217418_x_at | membrane-spanning 4-domains | 0.53879 | 0 |
| 212887_at | Sec23 homolog A (S. cerevisiae) | 0.66599 | 0 |
| 214093_s_at | NA | 0.64158 | 0 |
| 212623_at | KIAA0033 protein | 0.66508 | 0 |
| 213472_at | heterogeneous nuclear ribonucleoprotein H1 | 0.31249 | 0 |
| 219073_s_at | hypothetical protein FLJ20363 | 0.61979 | 0 |
| 209307_at | SWAP-70 protein | 0.6594 | 0.46576 |
| 207655_s_at | B-cell linker | 0.5885 | 0.46576 |
| 208691_at | transferrin receptor (p90, CD71) | 0.65934 | 0.46576 |
| 203579_s_at | solute carrier family 7, member 6 | 0.66266 | 0.46576 |
| 202169_s_at | aminoadipate-semialdehyde transferase | 0.6561 | 0.46576 |

TABLE 6-continued

Significantly downregulated genes in OA

| Gene ID | Gene Name | Fold Change | FDR (%) |
| --- | --- | --- | --- |
| 219667_s_at | hypothetical protein FLJ20706 | 0.6008 | 0.46576 |
| 202723_s_at | forkhead box O1A (rhabdomyosarcoma) | 0.59825 | 0.46576 |
| 217503_at | NA | 0.657687 | 1.117833 |
| 213461_at | cleavage and polyadenylation specific factor 5 | 0.652926 | 1.117833 |
| 213470_s_at | heterogeneous nuclear ribonucleoprotein H1 | 0.480516 | 1.117833 |
| 209257_s_at | chondroitin sulfate proteoglycan 6 | 0.629241 | 1.117833 |
| 221239_s_at | SH2 phosphatase anchor protein 1 | 0.64718 | 1.117833 |
| 219112_at | rap guanine nucleotide exchange factor | 0.603103 | 1.439049 |
| 211090_s_at | NA | 0.645879 | 1.439049 |
| 207072_at | interleukin 18 receptor accessory protein | 0.660589 | 1.439049 |
| 209753_s_at | thymopoietin | 0.633061 | 1.750521 |
| 204731_at | transforming growth factor, beta receptor III | 0.603254 | 1.750521 |
| 219497_s_at | B-cell CLL/lymphoma 11A (zinc finger protein) | 0.659726 | 1.750521 |
| 200952_s_at | cyclin D2 | 0.666066 | 1.750521 |
| 214447_at | v-ets erythroblastosis virus E26 oncogene homolog 1 | 0.493283 | 2.032423 |
| 214657_s_at | NA | 0.577381 | 2.862742 |
| 205321_at | eukaryotic translation initiation factor 2, subunit 3 | 0.511256 | 3.726109 |
| 211430_s_at | immunoglobulin heavy constant gamma 3 | 0.624618 | 3.989128 |

TABLE 7

Expression Predictors of OA subclasses

| Gene ID | Gene name |
| --- | --- |
| 205067_at | interleukin 1, beta |
| 202644_s_at | tumor necrosis factor, alpha-induced protein 3 |
| 201531_at | zinc finger protein 36, C3H type, homolog (mouse) |
| 201502_s_at | nuclear factor of kappa light polypeptide gene enhancer in B-cells inhibitor, alpha |
| 204440_at | CD83 antigen (activated B lymphocytes, immunoglobulin superfamily) |
| 217412_at | Human mRNA for T-cell receptor alpha-chain V-J-C, partial cds, clone WADM13D. |
| 202643_s_at | tumor necrosis factor, alpha-induced protein 3 |
| 212099_at | ras homolog gene family, member B |

Example 2

Further Marker Validation and Identification of Additional Markers 2.1. Peripheral Blood Leukocyte (PBL) Gene Expression Identifies a Subset of OA Patients with an Inflammatory Gene Signature.

PBL gene expression studies by microarray identified 332 upregulated genes and 193 downregulated genes in OA using a FDR of 5% and with at least a 1.25-fold change. To validate the hypothesis that pain and inflammation characterize a subset of OA patients with severe and progressive disease, a complete-linkage hierarchical clustering was performed to identify subclasses of OA based on the expression of 21 pre-selected inflammatory cytokine genes. Two subclasses of OA were identified: IL-1 and cytokine overexpressors ($OA^{IL-1}$) and an OA subset whose IL-1/cytokine gene expression profile did not differ from controls ($OA^{nl}$). The $OA^{IL-1}$ subclass had elevated levels of IL-1β (up 6.56-fold), IL-8 (up 2-fold), COX-2 (up 2.75-fold), and chemokines GROα (up 5.37-fold), macrophage inflammatory protein 1-alpha (MIP-1α) (up 6-fold) and MIP-1β (up 2.75-fold) compared to non-OA controls and the $OA^{nl}$. These findings (again controlling for BMI, age and gender) were validated in a separate population (OA patients from a Duke University POP cohort) (see Example 1 and Ref 1).

2.2. Association of OA PBL COX-2 Expression and Plasma PGE2 Production with Incidence and Severity of OA.

Figure 4:
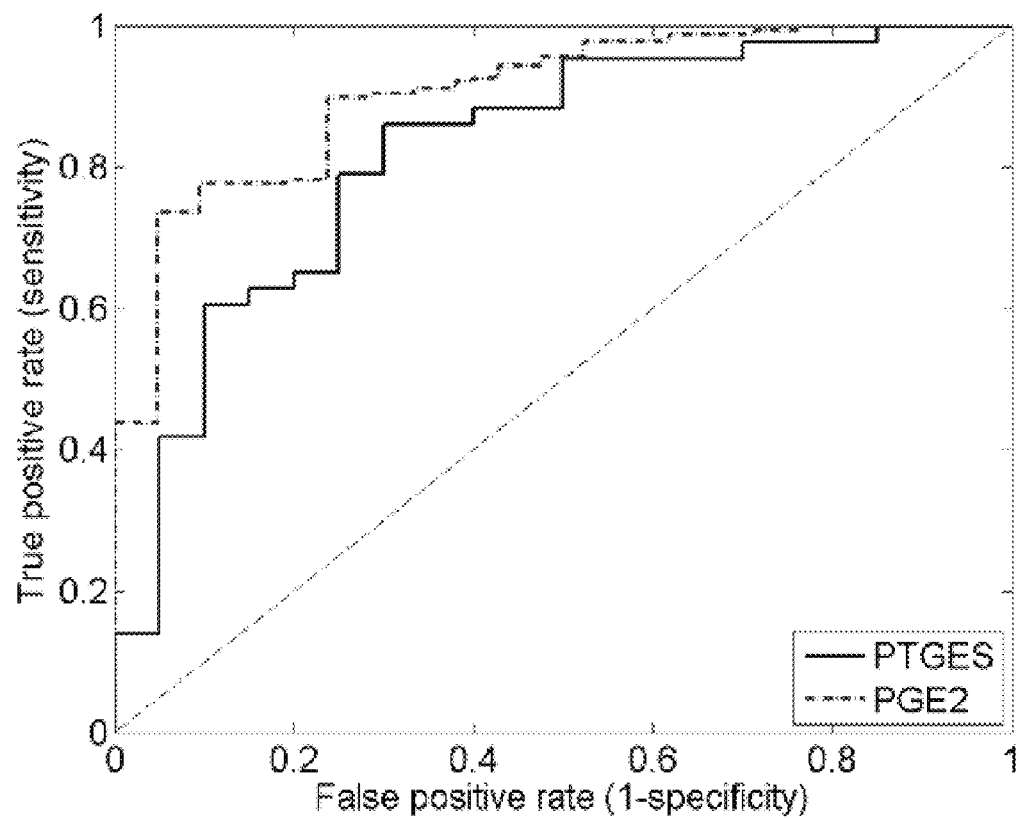
FIG. 4 shows receiver operating characteristic (ROC) curves: two predictors microarray PTGES gene probe sets (solid line, AUC=0.83) and ELISA PGE2 (dotted line, AUC=0.90) and their respective ROC curves are shown.

Using the support vector machine methodology (13) a combinatorial biomarker of OA was constructed based on microarray data of the NYUHJD Cohort. The biomarker based on probe sets representing PTGES members (PGE2 synthase and cyclooxygenase probe sets: 207388_s_at, 210367_s_at, 218083_at, 200627_at) could classify the case vs. control with 0.83 AUC (95% confidence interval 0.72-0.95, p<0.0001) (AUC: area under receiver operating characteristic (ROC) curve), as estimated by repeated 100 times 10-fold cross-validation protocol (14). The respective ROC curves are shown in FIG. 4.

Figure 5:
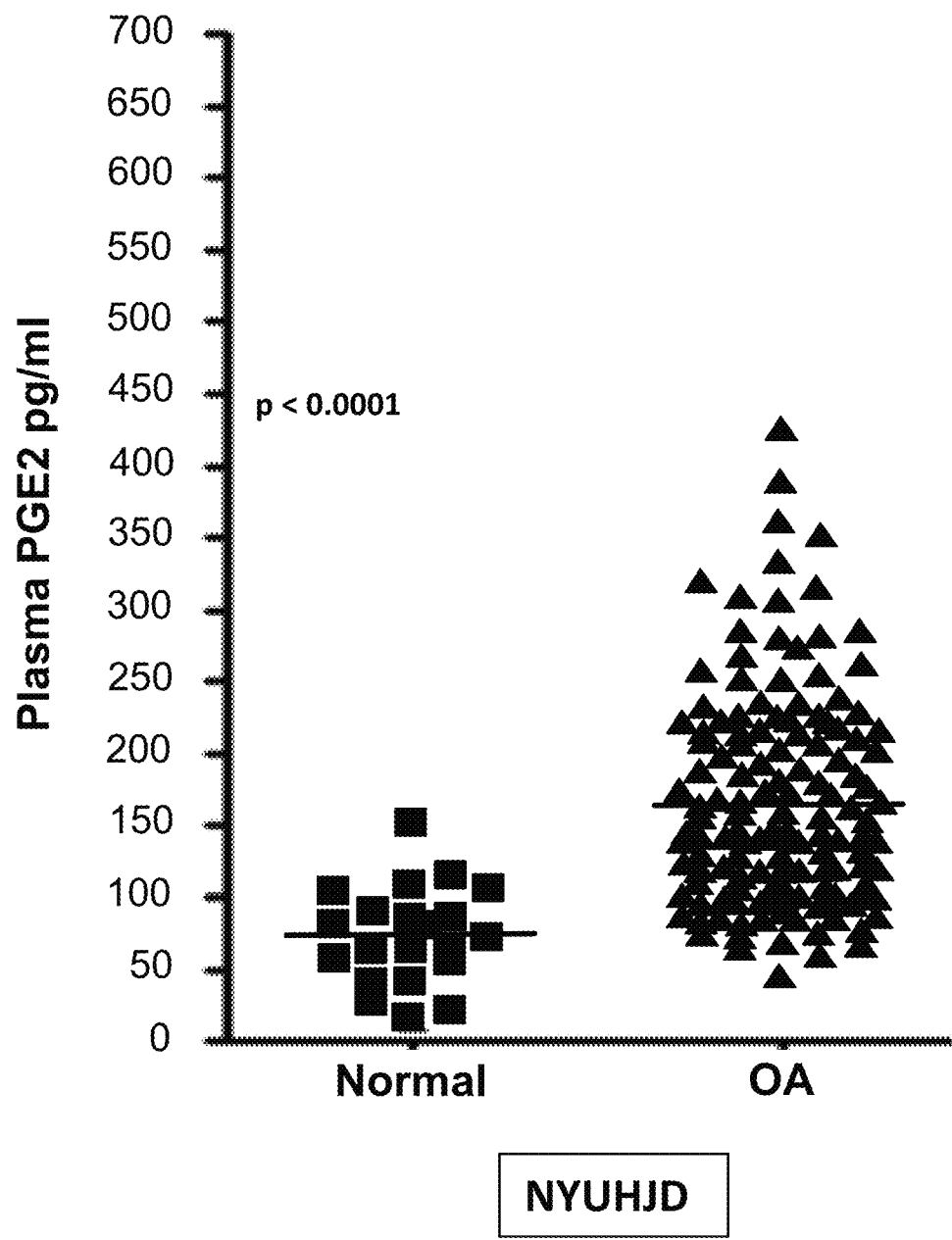
FIG. 5 shows increased plasma levels of PGE2, of symptomatic OA patients compared to mean age-matched healthy controls.

To validate the latter finding, the inventors considered whether the PGE2 signature estimated by ELISA in an independent cohort of 178 osteoarthritis cases and 21 healthy controls could classify case and control. In this cohort, the mean plasma PGE2 levels in OA patients was two-fold higher than in healthy controls (72.4±33.58 vs. 163±64.0 pg/ml, p=0.001) (FIG. 5). Similar to PTGES mRNA expression, plasma PGE2 biomarker was able to classify symptomatic osteoarthritis cases from controls with 0.90 AUC (95% confidence interval [0.84; 0.97] AUC, p<0.0001) (FIG. 4). Furthermore, to determine whether OA PBLs were "primed", PGE2 production was measured by whole blood PBL cultured (24 h) ex vivo. PGE2 in controls did not change, while levels in OA patients increased 300% over baseline (p<0.01) (15).

2.3. Predicting Osteoarthritis Severity.

The following 10 parameters have been measured for 128 patients: VAS pain, WOMAC score, plasma PGE2, plasma tMMP-9 (total MMP-9 including both pro and active form of MMP-9), plasma VEGF, plasma IL1-Ra, IL-1RN risk haplotypes CTA and TTG (representing alleles rs419598 (C/T), IL1RN rs315952 (T/T), rs9005 (A/G)) and PBL IL-1 and COX-2 mRNA expression.

Figure 6:
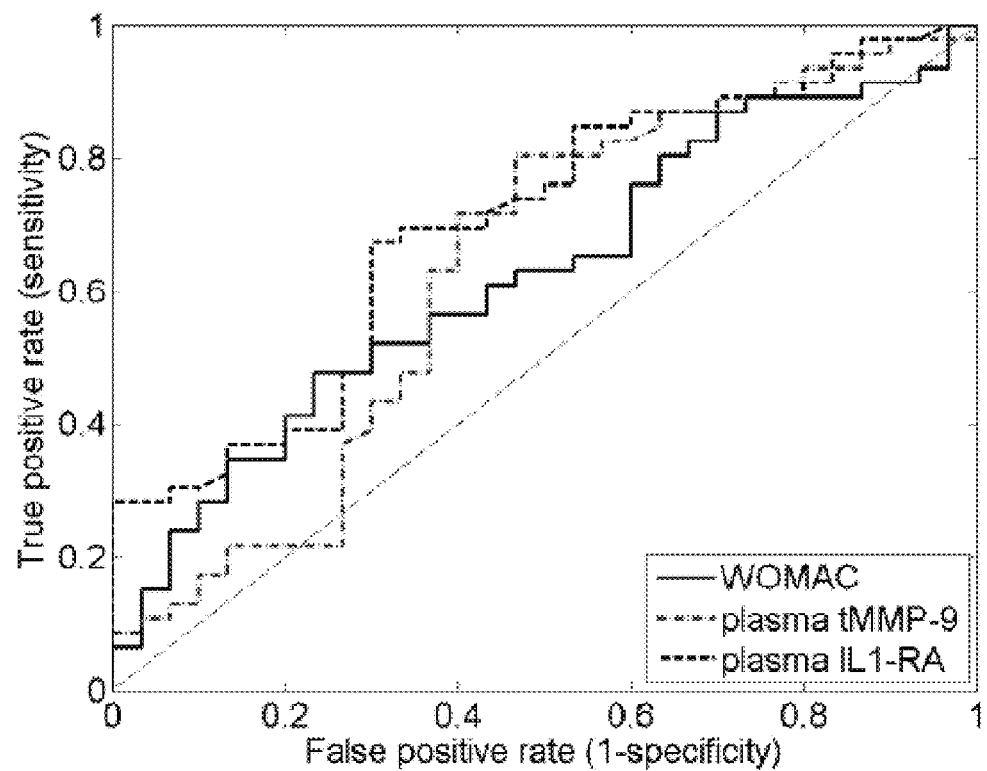
FIG. 6 shows receiver operating characteristic (ROC) curves. Three predictors—plasma total MMP-9 (dotted line, AUC=0.63, p=0.027), IL-1Ra (dotted black line, AUC=0.70, p=0.001), WOMAC score (solid line, AUC=0.62, p=0.028)—and their respective ROC curves are shown.

FIG. 6 illustrates three statistically significant predictors of severity (KL 1/2 vs. KL3/4) according to Delong's test for comparing areas under ROC curve at 0.05 α-level (7). All these three predictors retain statistical significance after correction for multiple comparisons using the FDR method of Storey (8).

When the above three statistically significant predictors were combined into a multivariate predictive model using kernel ridge regression (9,10), the resulting predictivity of radiographic severity increased to 0.71 AUC (95% confidence interval [0.59; 0.82] AUC, p-value=<0.001), as estimated by repeated 100 times 10-fold cross-validation protocol (6). In order to avoid overestimation of AUC due to selection of predictors, we verified that the same three statistically significant predictors were also obtained on the training subsets of the data during cross-validation (17).

These data demonstrate that a combinatorial approach allows prediction of radiographic severity fairly accurately but not significantly better than using only plasma IL-1Ra.

Additional plasma biomarker that correlated with knee OA severity was VEGF. Increased plasma levels of VEGF correlated negatively (-0.247) with JSW and positively (0.251) with KL score both at baseline and visit 24 month. However, VEGF did not correlate with knee OA progression (Table 8).

TABLE 8

| | p-value (correlation coefficient, positive/negative correlation) VEGF |
|---|---|
| JSW_baseline (signal) | 0.016 (−0.247) |
| JSW_24m (signal) | 0.017 (−0.244) |
| KL_baseline (signal) | 0.014 (0.251) |
| KL_24m(signal) | 0.003 (0.305) |
| JSW_delta_percent_all (signal) | 0.435 (0.081) |

TABLE 9

IL-1 overexpressors ($OA^{IL-1}$) associated with increased pain.

| | | Mean (standard deviation) | | |
|---|---|---|---|---|
| Measure | | $OA^{IL-1}$ (n = 74) | $OA^{nl}$ (n = 100) | p-value |
| WOMAC at baseline | sum pain | 45.32 (26.66) | 32.91 (20.89) | 0.004 |
| | sum stiffness | 52.99 (26.49) | 37.88 (24.71) | 0.001 |
| | sum phys fxn | 45.85 (23.92) | 32.83 (22.16) | 0.001 |
| | Total Score | 144.16 (71.88) | 103.6 (62.46) | 0.0001 |
| Pain VAS at baseline | Baseline | 55.16 (28.66) | 39.25 (27.26) | 0.001 |

TABLE 10

PBL IL-1 and, COX-2, and TNF-Alpha Over-expression and increased plasma total MMP-9 (tMMP9) are associated with progressive joint space narrowing at 24 months. Values are expressed as mean (SD).

| JSW (mm) signal | IL-1 | | | COX-2 | | | TNFα | | | Plasma tMMP9 | | |
|---|---|---|---|---|---|---|---|---|---|---|---|---|
| knee medial | $OA^{IL-1}$ (n = 71) | $OA^{nl}$ (n = 73) | p-value | $OA^{COX-2}$ (n = 71) | $OA^{nl}$ (n = 73) | p-value | $OA^{TNFa}$ (n = 74) | $OA^{nl}$ (n = 70) | p-value | >375 ng/ml (n = 65) | <375 ng/ml (n = 63) | p-value |
| baseline | 3.44 (1.80) | 3.07 (1.71) | 0.15 | 3.30 (1.89) | 3.2 (1.63) | 0.35 | 3.20 (1.89) | 3.31 (1.64) | 0.7097 | 3.04 (1.96) | 3.4 (1.62) | 0.196 |
| 24 month | 2.89 (1.83) | 2.99 (1.72) | 0.74 | 2.78 (1.83) | 3.11 (1.7) | 0.54 | 2.61 (1.87) | 3.29 (1.60) | 0.0198 | 2.47 (1.8) | 3.34 (1.65) | 0.014 |
| JSN signal | 0.55 (0.93) | 0.07 (1.01) | 0.007 | 0.52 (1.03) | 0.091 (0.92) | 0.007 | 0.59 (0.98) | 0.02 (0.93) | 0.0004 | 0.57 (0.93) | 0.069 (0.74) | 0.002 |

2.4. Predicting Osteoarthritis Progression: The Subset of OA with Increased IL-1, COX-2 Expression in Peripheral Blood Leukocyte (PBL) and with Elevated Plasma MMP-9 Overexpressors of SKOA is at Increased Risk for Radiographic Progression.

To determine whether increased PBL IL-1β expression ($OA^{IL-1}$) at baseline predicted risk for disease progression, patients were followed prospectively and delta change of KL and JSW was measured at 24 months. In an initial cohort of 78 patients, the increased expression of IL-1 was associated with increased JSN at 24 months (Example 1 and Ref 1). Additional data were collected for 146 OA patients who had both baseline and 24 month x-ray and IL-1 expression. This extended study confirms the initial finding that $OA^{IL-1}$ patients exhibited more joint space narrowing (JSN) at 24 months than the $OA^{nl}$ group (0.55 mm vs. 0.07, p<0.007) (Table 10). The mean JSW at baseline differed between $OA^{IL-1}$ (3.437 mm±1.8) and $OA^{nl}$ (3.07 mm±1.71) groups. Additionally, delta change of KL score in the $OA^{IL-1}$ group approached significance (p=0.1) compared to the $OA^{nl}$ group over 24 months. The subset characterized by increased PBL IL-1β expression ($OA^{IL-1}$) exhibited increased pain and an increased risk for disease progression at 24 months (Tables 9 and 10). Similarly, the subset characterized by increased PBL expression of TNF-α exhibited increased risk for disease progression at 24 months (Table 10).

In association studies, similar to the $OA^{IL-1}$ study described above, it was we explored whether elevated COX-2 expression in OA subsets associated with other clinical markers. We dichotomized OA patients were dichotomized based on median expression level of COX-2 and compared high COX-2 expressors ($OA^{COX-2}$) were compared with low COX-2 expressors ($OA^{nl}$). As shown in Table 10, mean JSW at baseline was similar in $OA^{COS-2}$ (3.41 mm±1.62) and $OA^{nl}$ (3.04±1.96) groups; however, the data indicate that $OA^{COX-2}$ patients exhibited more joint space narrowing (JSN) at 24 months than the $OA^{nl}$ group (0.57 vs. 0.07 mm, p<0.002) (Table 10).

As shown in Example 1, expression of MMP-9 is elevated in PBLs of OA compared to normal. The present inventors decided to test whether plasma levels of gelatinase(s) MMP-2 and 9 predict knee OA severity and progression based on radiographic findings. In the preliminary studies, it was observed that the mean plasma MMP-2 and -9 (pro and total) levels were 83.0±63.05 ng/ml, 30.7±32.64 ng/ml and 455.9±290.09 ng/ml, respectively. Only plasma total MMP-9 positively correlated with KL score both at baseline (r=0.220; p<0.036) and 24 months (r=0.249; p<0.015). MMP-2 or proMMP9 levels did not correlate with either radiographic marker. Patients were further dichotomized based on median value (375 ng/ml) of tMMP9 in OA plasma, which is 10-fold higher than reported normal plasma levels (20). Mean JSW at baseline was similar in OA patients who have greater than median tMMP9 (3.41 mm±1.62) and less than median (3.04 mm±1.96). However, as shown in Table 10, patients with tMMP9 above median level exhibited more joint space narrowing (JSN) at 24 months than other group (0.57 mm vs. 0.069, p<0.002) (Table 10). These data provide evidence that genomic biomarkers, specifically increased IL-1β and COX-2 expression by peripheral blood leukocytes and plasma MMP-9, identify a subset of OA patients at increased risk for disease progression.

2.5. Predictors of Joint Space Narrowing (JSN).

As shown herein, pain and inflammation characterize a subset of osteoarthritis with progressive disease (dichotomized at 0.2 and 0.6 mm). The inventors then attempted to predict slow and fast progressors (dichotomized at 0.2 and 0.6 mm) based on medial joint space narrowing (JSN) using 10 predictors as described above (as continuous variables).

Table 11 displays four statistically significant predictors (among 10 predictors) of JSW medial progression dichotomized at 0.2 mm according to Delong's test for comparing areas under ROC curve at 0.05 α-level (21). All four predictors retain statistical significance after correction for multiple comparisons using the FDR method of Storey (22).

TABLE 11

| Predictor | Area under ROC curve (AUC) | p-value | q-value (FDR) |
|---|---|---|---|
| Plasma tMMP-9 | 0.66 | 0.002 | 0.011 |
| Plasma IL1-RA | 0.63 | 0.017 | 0.026 |
| TTG genotype | 0.59 | 0.035 | 0.039 |
| COX2 expression | 0.65 | 0.005 | 0.011 |

When the above four statistically significant predictors were combined into a multivariate predictive model using kernel ridge regression (23;24), the resulting predictivity of JSW medial progression increased to 0.74 AUC (95% confidence interval [0.63; 0.84] AUC, p-value=<0.001), as estimated by repeated 100 times 10-fold cross-validation protocol (14). In order to avoid overestimation of AUC due to selection of predictors, it was verified that the same four statistically significant predictors were also obtained on the training subsets of the data during cross-validation (17). These data demonstrate that a combinatorial approach allows prediction of JSW medial progression fairly accurately and better than using any of the ten predictors alone.

Additionally, prediction of JSW medial progression dichotomized at 0.6 mm proves to be a more challenging task than using 0.2 mm dichotomization threshold but still yields statistically significant results. Specifically, two predictors are univariately statistically significant at 0.05 α-level according to Delong's test for comparing areas under ROC curve (21): plasma tMMP-9 (AUC=0.65, p-value=0.006) and IL1 expression (AUC=0.61, p-value=0.034). Interestingly, only plasma tMMP-9 with q-value=0.031 retains statistical significance after correction for multiple comparisons using the FDR method of Storey (22) at 0.05 q-value threshold. IL1 expression results in q-value=0.079 which is above 0.05 threshold. When these two predictors are combined into a multivariate predictive model using either of tested supervised classification methods (support vector machines, logistic regression, kernel ridge regression, CART) (23;24), the predictivity of JSW medial progression, as estimated by repeated 100 times 10-fold cross-validation protocol (14), did not increase compared to 0.65 AUC value of plasma tMMP-9 (the best univariate predictor).

The above data demonstrate that a combinatorial approach allows prediction of both slow (0.2 mm) and fast (0.6 mm) progressive JSN fairly accurately using plasma tMMP9 levels. In conclusion, there is increased inflammatory mediator gene expression (COX-2, IL-1β, TNF-α), protease and elevated plasma levels of PGE2 in OA patients compared to age-matched controls. The data indicate that inflammatory events within joint tissues of patients with SKOA are reported in peripheral blood.

REFERENCE LIST (1) Attur M, Belitskaya-Levy I, Oh C, Krasnokutsky S, Greenberg J, Samuels J et al. Increased interleukin-1beta gene expression in peripheral blood leukocytes is associated with increased pain and predicts risk for progression of symptomatic knee osteoarthritis. Arthritis Rheum 2011; 63(7):1908-17.

(2) Krasnokutsky S, Belitskaya-Levy I, Bencardino J, Samuels J, Attur M, Regatte R et al. Quantitative MRI evidence of synovial proliferation is associated with radiographic severity of knee osteoarthritis. Arthritis Rheum 2011; Jun 6. doi: 10.1002/art.30471. [Epub ahead of print].

(3) Kerkhof H J M, Doherty M, Arden NK, Abramson S B, Attur M, Bos S D et al. Large-scale meta-analysis of interleukin-1 beta and interleukin-1 receptor antagonist polymorphisms on risk of radiographic hip and knee osteoarthritis and severity of knee osteoarthritis. Osteoarthritis Cartilage 2011; 19(3):265-71.

(4) Attur M, Wang H Y, Kraus V B, Bukowski J F, Aziz N, Krasnokutsky S et al. Radiographic severity of knee osteoarthritis is conditional on interleukin 1 receptor antagonist gene variations. Ann Rheum Dis 2010; 69(5):856-61.

(5) Attur M, Krasnokutsky S, Belitskaya-Levy I, Dave M, Patel J, Samuels J et al. Elevated levels of inflammatory mediator prostaglandin E2 (PGE2) in ex-vivo cultured peripheral blood leukocytes (PBL) of osteoarthritis (OA) patients. [abstract]. Arthritis Rheum 58[Suppl], 5495. 2008.
  Ref Type: Abstract (6) Attur M, Dave M, Patel J, Al-Mussawir H, Palmer G, Pillinger M H et al. PGE2 attenuates aggrecan gene expression and accelerates aggrecan degradation via activion of ADAMTS in OA chondrocytes. Osteoarthritis Cartilage 15[Suppl 3], C102-C103. 2007.
  Ref Type: Abstract (7) Attur M, Oh C, Krasnokutsky S, Samuels J, Rybak L, Bencardino J et al. Interleukin-1 receptor antagonist gene variations predict the severity and progression of knee osteoarthritis. [abstract]. Osteoarthritis Cartilage 18[Suppl 2], 5172. 2010.
  Ref Type: Abstract (8) Attur M, Bukowski J F, Wang H Y, Aziz N, Kornman K S, Krasnokutsky S et al. Genetic markers associated with generalized osteoarthritis (GOA). [abstract]. Osteoarthritis Cartilage 16[Suppl 4], 5158. 2008.
  Ref Type: Abstract (9) Attur M, Kerkhof H, Oh C, Krasnokutsky S, Samuels J, Uitterlinden A G et al. Association of interleukin-1 receptor antagonist (IL-1RN) TTG haplotype with radiographic knee OA severity in large scale meta-analysis. [abstract]. Osteoarthritis Cartilage 18[Suppl 2], 5172. 2010.
Ref Type: Abstract
(10) Regatte R, Krasnokutsky S, Samuels J, Rosenthal P, Abellana V, Greenberg J et al. Bone marrow changes (edema and fatty infiltration) on MRI predict radiographic severity of knee OA. [abstract]. Osteoarthritis Cartilage 15[Suppl C], C29-C30. 2007.
Ref Type: Abstract
(11) Bukowski J F, Wang H Y, Aziz N, Krasnokutsky S, Samuels J, Greenberg J et al. IL-1 RN polymorphisms are associated with radiographic severity in osteoarthritis. [abstract].
Osteoarthritis Cartilage 16[Suppl 4], S34. 2008.
Ref Type: Abstract
(12) Lai Y, Yu X P, Zhang Y, Tian Q, Song H, Mucignat M T et al. Enhanced COMP catabolism detected in serum of patients with arthritis and animal models through a novel capture ELISA. [abstract]. Osteoarthritis Cartilage in press. 2011.
Ref Type: Abstract
(13) Vapnik V N. Statistical learning theory. New York: Wiley; 1998.
(14) Braga-Neto U M, Dougherty E R. Is cross-validation valid for small-sample microarray classification? Bioinformatics 2004; 20(3):374-80.
(15) Attur M, Krasnokutsky S, Belitskaya-Levy I, Dave M, Patel J, Samuels J et al. Elevated levels of inflammatory mediator prostaglandin E2 (PGE2) in ex-vivo cultured peripheral blood leukocytes (PBL) of osteoarthritis (OA) patients. [abstract]. Osteoarthritis Cartilage 16[Suppl 4], 5191. 2008.
Ref Type: Abstract
(16) Nemirovskiy O, Buck R, Sunyer T, Abrams M, Aggarwal P, Dufield D et al. Predicting radiographic joint space narrowing (JSN) using biomarkers for osteoarthritis (OA) clinical trials. [abstract]. Osteoarthritis Cartilage 16[Suppl 4], S56-S57. 2008.
Ref Type: Abstract
(17) Simon R, Radmacher M D, Dobbin K, McShane L M. Pitfalls in the use of DNA microarray data for diagnostic and prognostic classification. J Natl Cancer Inst 2003; 95(1):14-8.
(18) Lee J, Banu S K, Subbarao T, Starzinski-Powitz A, Arosh J A. Selective inhibition of prostaglandin E2 receptors EP2 and EP4 inhibits invasion of human immortalized endometriotic epithelial and stromal cells through suppression of metalloproteinases. Mol Cell Endocrinol 2011; 332(1-2):306-13.
(19) Attur M, Al-Mussawir HE, Patel J, Kitay A, Dave M, Palmer G et al. Prostaglandin E2 exerts catabolic effects in osteoarthritis cartilage: evidence for signaling via the EP4 receptor. J Immunol 2008; 181(7):5082-8.
(20) Jonsson S, Lundberg A, Kalvegren H, Bergstrom I, Szymanowski A, Jonasson L. Increased levels of leukocyte-derived MMP-9 in patients with stable angina pectoris. PLoS One 2011; 6(4):e19340.
(21) DeLong E R, DeLong D M, Clarke-Pearson D L. Comparing the areas under two or more correlated receiver operating characteristic curves: a nonparametric approach. Biometrics 1988; 44(3):837-45.
(22) Storey J D. A direct approach to false discovery rates. Journal of the Royal Statistical Society Series B, Statistical Methodology 2002; 64(Part 3):479-98.
(23) Hastie T, Tibshirani R, Friedman J H. *The elements of statistical learning: data mining, inference, and prediction*. New York: Springer; 2001.
(24) Shawe-Taylor J, Cristianini N. *Kernel methods for pattern analysis*. Cambridge, UK: Cambridge University Press; 2004.

\* \* \*

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

All patents, applications, publications, test methods, literature, and other materials cited herein are hereby incorporated by reference in their entirety as if physically present in this specification.

What is claimed is:

1. A method for treating osteoarthritis in a subject, wherein the subject has been diagnosed with osteoarthritis but does not have severe osteoarthritis, said method comprising the steps of:
   (a) measuring in a blood plasma sample obtained from the subject the plasma level of one or more protein(s) selected from the group consisting of total matrix metalloproteinase 9 (tMMP-9), proMMP-9 (pMMP-9), and interleukin-1 receptor antagonist (IL1-Ra); and
   (b) administering an osteoarthritis treatment to the subject whose plasma level of one or more protein(s) selected from the group consisting of tMMP-9, pMMP-9, and IL1-Ra is increased by at least 2 fold as compared to a control plasma level(s) of said protein(s).

2. The method of claim 1, wherein the subject has been diagnosed with knee osteoarthritis and has a Kellgren-Lawrence (KL) score of 1-3 in at least one knee.

3. The method of claim 2, wherein the subject has joint space width (JSW) of 3.8±1.7 mm.

4. The method of claim 1, wherein the subject is human.

5. The method of claim 1, wherein the blood plasma sample obtained from the subject has been prepared in the presence of heparin.

6. The method of claim 1, wherein the plasma level of the protein(s) is determined using ELISA.

7. The method of claim 1, wherein the control plasma level of said protein(s) is a plasma level of said protein(s) in a similarly processed plasma sample from a control subject or a mean level of several control subjects.

8. The method of claim 7, wherein the control subject (i) is matched to the tested subject by Body Mass Index (BMI) and/or age and/or gender and (ii) does not have osteoarthritis as determined by both radiographic and symptomatic examination.

9. The method of claim 1, wherein the control plasma level of said protein(s) is a predetermined standard.

10. A method for treating osteoarthritis in a subject, the method comprising administering an osteoarthritis treatment to a subject with elevated plasma level of one or more protein(s) selected from the group consisting of total matrix metalloproteinase 9 (tMMP-9), proMMP-9 (pMMP-9), and interleukin-1 receptor antagonist (IL1-Ra), wherein the subject does not have severe osteoarthritis.

11. The method of claim 10, wherein the subject has been diagnosed with knee osteoarthritis and has a Kellgren-Lawrence (KL) score of 1-3 in at least one knee.

12. The method of claim 11, wherein the subject has joint space width (JSW) of 3.8±1.7 mm.

13. The method of claim 10, wherein the subject is human.

14. A method for determining whether a subject diagnosed with osteoarthritis is at increased risk for progression to severe osteoarthritis within 12-24 months, said method comprising the steps of:
(a) preparing a blood plasma sample obtained from the subject in the presence of heparin;
(b) measuring in the blood plasma sample prepared in step (a) a plasma level of one or more protein(s) selected from the group consisting of total matrix metalloproteinase 9 (tMMP-9), proMMP-9 (pMMP-9), and interleukin-1 receptor antagonist (IL1-Ra);
(c) comparing the plasma level(s) measured in step (b) to a control plasma level(s) of said protein(s), and (d) identifying the subject as being at increased risk for progression to severe osteoarthritis within 12-24 months when the plasma level of one or more protein(s) selected from the group consisting of tMMP-9, pMMP-9, and IL1-Ra in step (b) is increased by at least 2 fold as compared to the control plasma level(s) of said protein(s).

15. The method of claim 14, wherein the plasma level of the protein(s) is determined using ELISA.

16. The method of claim 14, wherein the control plasma level of said protein(s) is a plasma level of said protein(s) in a similarly processed plasma sample from a control subject or a mean level of several control subjects.

17. The method of claim 16, wherein the control subject (i) is matched to the tested subject by Body Mass Index (BMI) and/or age and/or gender and (ii) does not have osteoarthritis as determined by both radiographic and symptomatic examination.

18. The method of claim 14, wherein the control plasma level of said protein(s) is a predetermined standard.

19. The method of claim 14, comprising collecting the blood sample from the subject into a heparinized tube.

20. The method of claim 14, wherein the subject is human.

21. The method of claim 14, wherein the osteoarthritis is a knee osteoarthritis.

22. The method of claim 21, wherein the subject has a Kellgren-Lawrence (KL) score of 1-3 in at least one knee.

23. The method of claim 22, wherein the subject has joint space width (JSW) of 3.8±1.7 mm.

* * * * *